US006631333B1

(12) United States Patent
Lewis et al.

(10) Patent No.: US 6,631,333 B1
(45) Date of Patent: Oct. 7, 2003

(54) METHODS FOR REMOTE CHARACTERIZATION OF AN ODOR

(75) Inventors: Nathan S. Lewis, Pasadena, CA (US); Erik Severin, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 328 days.

(21) Appl. No.: 09/596,758

(22) Filed: Jun. 15, 2000

Related U.S. Application Data

(63) Continuation-in-part of application No. 09/568,784, filed on May 10, 2000, which is a continuation-in-part of application No. 09/409,644, filed on Oct. 1, 1999.
(60) Provisional application No. 60/140,027, filed on Jun. 16, 1999, and provisional application No. 60/133,318, filed on May 10, 1999.

(51) Int. Cl.[7] .............................................. G01N 27/12
(52) U.S. Cl. .......................................... 702/24; 702/23
(58) Field of Search ........................ 73/23, 23.2, 23.3, 73/23.34, 31.05, 25.01; 205/787; 364/496, 497; 422/82.2, 95, 98; 436/147, 151, 43; 702/22, 23, 24, 30

(56) References Cited

U.S. PATENT DOCUMENTS

| | | | | |
|---|---|---|---|---|
| 4,517,161 A | * | 5/1985 | Gravina et al. ................ 422/95 |
| 4,555,930 A | * | 12/1985 | Leach et al. ..................... 73/23 |
| 4,847,783 A | * | 7/1989 | Grace et al. ................. 364/497 |
| 4,895,017 A | * | 1/1990 | Pyke et al. ...................... 73/23 |
| 5,469,369 A | * | 11/1995 | Rose-Pehrsson et al. ... 364/497 |
| 5,494,826 A | * | 2/1996 | Stetter et al. ................ 436/147 |
| 5,526,280 A | * | 6/1996 | Consadori et al. .......... 364/496 |
| 6,093,308 A | * | 7/2000 | Lewis et al. ................. 205/787 |
| 6,170,318 B1 | * | 1/2001 | Lewis ........................ 73/23.34 |
| 6,182,497 B1 | * | 2/2001 | Krajci ......................... 73/23.2 |
| 6,244,096 B1 | * | 6/2001 | Lewis et al. ................. 73/23.2 |
| 6,290,911 B1 | * | 9/2001 | Lewis et al. .............. 422/82.02 |
| 6,315,956 B1 | * | 11/2001 | Foulger ........................ 422/98 |
| 6,408,250 B1 | * | 6/2002 | Grate et al. .................... 702/30 |
| 6,455,319 B1 | * | 9/2002 | Lewis et al. ................. 436/151 |
| 6,467,333 B2 | * | 10/2002 | Lewis et al. ................ 73/31.05 |

OTHER PUBLICATIONS

Nakamoto, T; Ishida, H; Moriizumi, T;"Active Odor Sensing System"; Proceedings of IEEE International Symposium on Industrial Electronics; vol. 1; 1997; pp SS128–SS133.*
Mitrovics, J; Ulmer, H; Noetzel, G; Weimar, U; Gopel, W;"Hybrid Modular Sensor Systems: A New Generation of Electronic Noses"; Proceedings of the IEEE International Symposium on Industrial Electronics; vol. 1; 1997; SS116–SS121.*
Keller, P; Kangas, L; Linden, L; Hashem, S; Kouzes, R; "Electronic Noses and Their Applications"; IEEE Technical Applications Conference and Workshops Northcon 95; 1995; pp 116.*
Nagle, H; Gutierrez–Osuna, R; Schiffman, S;"The How and Why of Electronic Noses"; IEEE Spectrum; vol. 35 Issue 9; 1998; pp 22–31.*
Harris, P; Andrews, M; Partridge, A;"Conductive Polymer Sensor Measurements"; International Conference on Solid State Sensors and Actuators; vol. 2; 1997, pp 1063–1066.*
Shurmer, H;"The Fifth Sense—on the Scent of the Electronic Nose"; IEEE Review; vol. 36 Issue 3; 1990; pp 95–98.*

* cited by examiner

*Primary Examiner*—John Barlow
*Assistant Examiner*—Douglas N Washburn
(74) *Attorney, Agent, or Firm*—Fish & Richardson P.C.

(57) ABSTRACT

Provided are compositions and systems useful in remote monitoring of chemical hazards, air quality, and medical conditions, for example, robotic systems to search for and detect explosives, mines, and hazardous chemicals. In addition, the methods, systems and compositions of the invention provide the ability to mine data from a database containing a plurality of chemical fingerprints.

31 Claims, 5 Drawing Sheets

METHODS FOR REMOTE CHARACTERIZATION OF AN ODOR

CROSS REFERENCE TO RELATED APPLICATIONS

This application claims priority under 35 U.S.C. §119(e)(1) to U.S. Provisional Application No. 60/140,027, filed Jun. 16, 1999, and is a continuation-in-part under 35 U.S.C. §120 to U.S. patent application Ser. No. 09/568,784, filed May 10, 2000, entitled, "Use of Spatiotemporal Response Behaviour in Sensor Arrays to Detect Analytes in Fluids," which application claims priority under 35 U.S.C. §119(e)(1) from Provisional Application Serial No. 60/133,318, filed May 10, 1999 and U.S. Provisional Application No. 60/140,027, filed Jun. 16, 1999, and is a continuation-in-part under 35 U.S.C. §120 to U.S. application Ser. No. 09/409,644, filed Oct. 1, 1999, all of which are incorporated herein by reference in their entirety.

The U.S. Government may have certain rights in this invention. This invention was made in part from Grant Nos. DAAK-60-97-K-9503 awarded by the Defense Advanced Research Projects Agency (DARPA) and DAAG-55-97-1-1087 awarded by the Army Research Office.

FIELD OF THE INVENTION

The present invention generally relates to remote analysis of analytes and more particularly remote analysis of analytes present in the vapor or odor phase of a sample.

BACKGROUND

There is considerable interest in developing sensors that act as analogs of the mammalian olfactory system (Lundstrom et al., Nature 352:47–50, 1991; Shurmer and Gardner, Sens. Act. B 8:1–11, 1992; Shurmer and Gardner, Sens. Actuators B 15:32, 1993). Such sensors have proven useful in the detection of small molecules and odorants.

Such broadly responsive sensor arrays have exploited heated metal oxide thin film resistors (Gardner et al., Sens. Act. B4:117–121, 1991; Gardner et al., Sens. Act. B 6:71–75, 1991), polymer sorption layers on the surfaces of acoustic wave resonators(Grate and Abraham, Sens. Act. B 3:85–111, 1991; Grate et al., Anal. Chem. 65:1868–1881, 1993), arrays of electrochemical detectors (Stetter et al., Anal. Chem. 58:860–866, 1986; Stetter et al., Sens. Act. B 1:43–47, 1990; Stetter et al., Anal. Chem. Acta 284:1–11, 1993), conductive polymers or composites that consist of regions of conductors and regions of insulating organic materials (Pearce et al., Analyst 118:371–377, 1993; Shurmer et al., Sens. Act. B 4:29–33, 1991; Doleman et al., Anal. Chem. 70:2560–2654, 1998; Lonergan et al., Chem. Mater. 8:2298, 1996). Arrays of metal oxide thin film resistors, typically based on tin oxide ($SnO_2$) films that have been coated with various catalysts, yield distinct, diagnostic responses for several vapors (Corcoran et al., Sens. Act. B 15:32–37, 1993). Surface acoustic wave resonators are sensitive to both mass and acoustic impedance changes of the coatings in array elements, but the signal transduction mechanism involves somewhat complicated electronics, requiring frequency measurement to 1 Hz while sustaining a 100 MHZ Rayleigh wave in the crystal. Attempts have also been made to construct arrays of sensors with conducting organic polymer elements that have been grown electrochemically through use of nominally identical polymer films and coatings. Moreover, Pearce et al., Analyst 118:371–377, 1993; and Gardner et al., Sensors and Actuators B 18–19:240–243, 1994, describe, polypyrrole based sensor arrays for monitoring beer flavor. Shurmer (1990) U.S. Pat. No. 4,907,441, describes general sensor arrays with particular electrical circuitry. U.S. Pat. No. 4,674,320 describes a single chemoresistive sensor having a semi-conductive material selected from the group consisting of phthalocyanine, halogenated phthalocyanine and sulfonated phthalocyanine, which was used to detect a gas contaminant. Other gas sensors have been described by Dogan et al., Synth. Met. 60:27–30, 1993; and Kukla, et al. Films. Sens. Act. B., Chemical 37:135–140, 1996.

Measurement of air content for the detection of contaminants has become a growing concern both in the workplace (e.g., factories and laboratories), as well as in residential neighborhoods and homes. Currently, detection of hazardous chemicals or air contaminants is the result of reactions by humans and animals which are sensitive to the analyte. Upon detection, hazardous chemical teams or air-quality specialists are mobilized to the area of contamination with specialized equipment for collecting the analyte. The readings are then collected manually and often the sample is then physically taken to a separate location for analysis. These current methods require hazardous materials teams to physically enter the area and submit themselves to risks associated with the hazard.

In addition, breath testing has long been recognized as a non-intrusive medical technique that allows for diagnosis of disease or the presence of analytes. Medical symptoms of many types of conditions can be difficult to detect by medical professionals or their detection requires costly, time consuming, and highly invasive procedures often resulting in lost man hours at work, and increased risks of mortality and morbidity. Currently, medical diagnostics such as blood pressure readings and glucose readings are taken at doctors' offices or blood laboratories. The readings are then collected manually and depend on the patient's state of health at that particular time. In some cases, individuals take readings at home to assist doctors to better determine medication identification and levels. This data depends on the patient's proficiency and accuracy at taking readings, and is hard for the physician to analyze and is normally communicated only at a doctor's visit. Typically, the patient is diagnosed and medicated based on a minimum amount of data and analysis, which furthermore is not presented to the doctor in a format that facilitates diagnosis. Each reading is presented by an individual manually listing out his own readings with the date and time that these readings are taken—often in irregular intervals.

Diagnosis of many types of medical conditions, such as hypoglycemia and diabetes mellitus, can be markedly improved by a system to consolidate the data and present the data in a format which facilitates such diagnosis. In addition, remote monitoring of chemical hazard reduces the risk associated with local detection.

SUMMARY OF THE INVENTION

The present invention provides compositions and systems useful in remote monitoring of chemical hazards, air quality, and medical conditions, for example, robotic systems to search for and detect explosives, mines, and hazardous chemicals. In addition, the methods, systems and compositions of the invention provide the ability to mine data from a database containing a plurality of chemical fingerprints.

Accordingly, in one embodiment, the present invention is used with subjects who may have a medical condition such as, for example, diabetes mellitus to improve diagnosis and treatment of medical disorders more accurately and to assist medical practitioners in determining the proper amount of medication or other treatment to prescribe. The term "medical practitioner" is intended to include any individual who treats, or prescribes treatment to another individual to improve the latter's health or well-being. One embodiment of the invention is to gather, organize, and present data which may be collected over a long period of time in a way that best facilitates accurate diagnosis and proper treatment of such medical conditions which can require long-term profiling of medical readings.

In one embodiment, a method for remote characterization of a gaseous or vapor sample is provided. The method includes contacting at least one sensor with a gaseous or vapor sample, wherein the sample contains at least one analyte, the sensor providing a detectable signal when contacted by the analyte, transmitting data corresponding to the detectable signal to a remote location, analyzing the data received at the remote location, and identifying the analyte present in the gaseous or vapor sample thereby characterizing the sample.

In another embodiment, the invention provides a sensor array system f6r remote characterization of a gaseous or vapor sample. The system includes at least one sensor, wherein the sensor provides a detectable signal when contacted by an analyte; a measuring apparatus, in communication with the sensor capable of measuring the detectable signal; a transmitting device, in communication with the measuring apparatus for transmitting information corresponding to the detectable signal to a remote location; and a computer comprising a resident algorithm capable of characterizing the analyte.

In yet another embodiment, the invention provides a method for remote characterization of a disease in a subject. The method includes contacting at least one sensor with a gaseous or vapor sample obtained from the subject, wherein the sensor provides a detectable signal when contacted by an analyte present in the sample. In one embodiment the sensor has regions of a conductive material and regions of a material compositionally different than the conductive material, and wherein the materials provide an electrical path through the regions of conductive material and compositionally different material of the sensor, wherein interaction of the analyte with the sensor changes the resistance of the sensor. Electrically measuring the change in resistance as a detectable signal of the sensor, transmitting data corresponding to the detectable signal to a remote location; analyzing the data received at the remote location; and identifying the analyte present in the gaseous or vapor sample thereby characterizing the disease.

In yet another embodiment, the invention provides a method of monitoring trends across populations or changes in a physical state of a subject over a period of time. The method includes contacting at least one sensor with a gaseous or vapor sample obtained from the subject at two or more time points, wherein the sensor provides a detectable signal when contacted by an analyte present in the sample, transmitting data corresponding to the detectable signal to a remote location; analyzing the data received at the remote location; and identifying a change in an analyte present in the gaseous or vapor sample.

DETAILED DESCRIPTION OF THE INVENTION

Figure 1A:
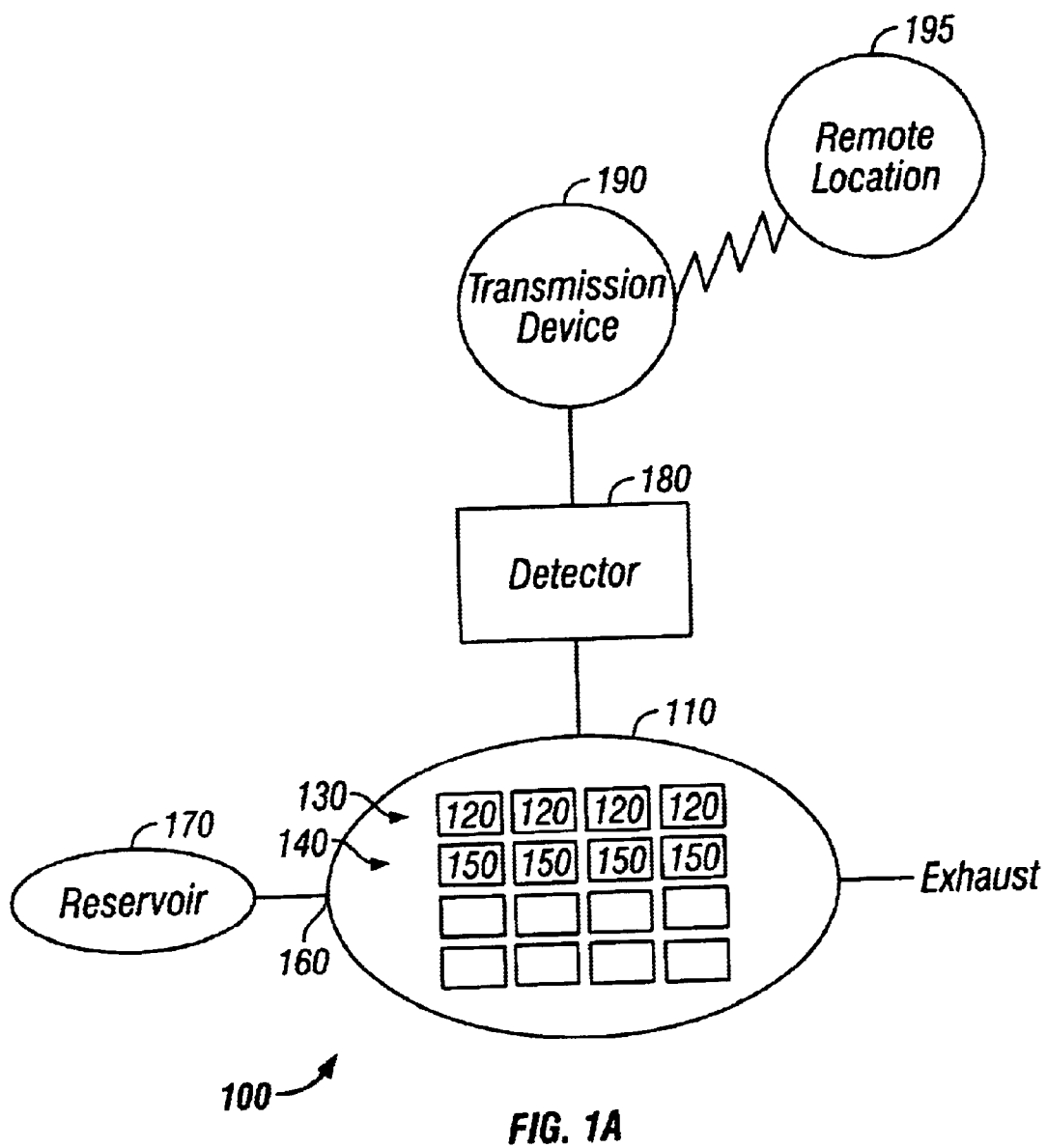
FIG. 1(A) is a block diagram illustrating a remote odor analysis system.

There is a need for a mechanism to transmit identifying information on various smells (e.g., vapor or gaseous analytes) remotely, for example, over the Internet. Examples of technology include the use of MPEG and streaming video, for example, and Real Audio and other similar sound data files which are sent remotely, however, there currently is no system for remotely transmitting or identifying olfactory information. Such information would be of value in a plethora of applications. For example, the ability to transmit information about and/or allow identification or classification of an odor present in a patient's breath could be readily transmitted over the Internet, an intranet, or other analog or digital information transfer system, the information could be analyzed remotely and used for diagnostic purposes by a physician accessing the information at a remote site from the patient. Similarly, local environmental information concerning the odors present at a monitoring site might be used to ascertain the appearance of a noxious or toxic substance in the atmosphere through remote analysis, either human-performed or automatically, of the signatures of the odorant. Described herein are methods and systems for satisfying this outstanding need.

In one approach, an array of broadly cross-reactive chemically-sensitive sensors is utilized. Upon exposure to an odorant, the array generates a detectable signal, pattern or fingerprint either electrically, optically, acoustically, or combinations thereof, in form. The form of the array signatures depends on the chemical characteristics of the sensors, which may be dye-impregnated coatings that change color upon exposure to an analyte, conductive polymer composites that change their electrical impedance properties upon exposure to the odorant, cantilever-based transducers coated with different polymeric films that produce a series of deflections that are translated into voltages outputted by the array, and the like.

Following generation of the detectable signal(s), the signal(s) can be coverted into a digital pattern that becomes characteristic of that odorant and/or background conditions during the analysis interval. A digitized signature can then be transmitted across an information network digitally and analyzed remotely, or partially compressed and/or analyzed locally before transmission. The data can then be decompressed and subjected to further analysis either automatically or manually at the remote site.

Examples of some specific uses of the invention include having subjects having or at risk of having a medical condition present a breath sample to a set of sensors and having the resultant signature transmitted across an information network from a location that is different from the medical practitioner, who then observes the pattern and interprets it to diagnose a patient's condition (with or without the aid of automated data analysis algorithms either before or after transmission of the information along the network); monitoring local sites from a remote station to identify the local environmental conditions as a function of time; obtaining historical records of the typical background odorant profiles of certain locations for comparison at later dates to validate the presence of pollution from neighboring facilities that have initiated objectionable or possibly hazardous operating procedures that affect the vapor environment in the vicinity; and the like.

Figure 1B:
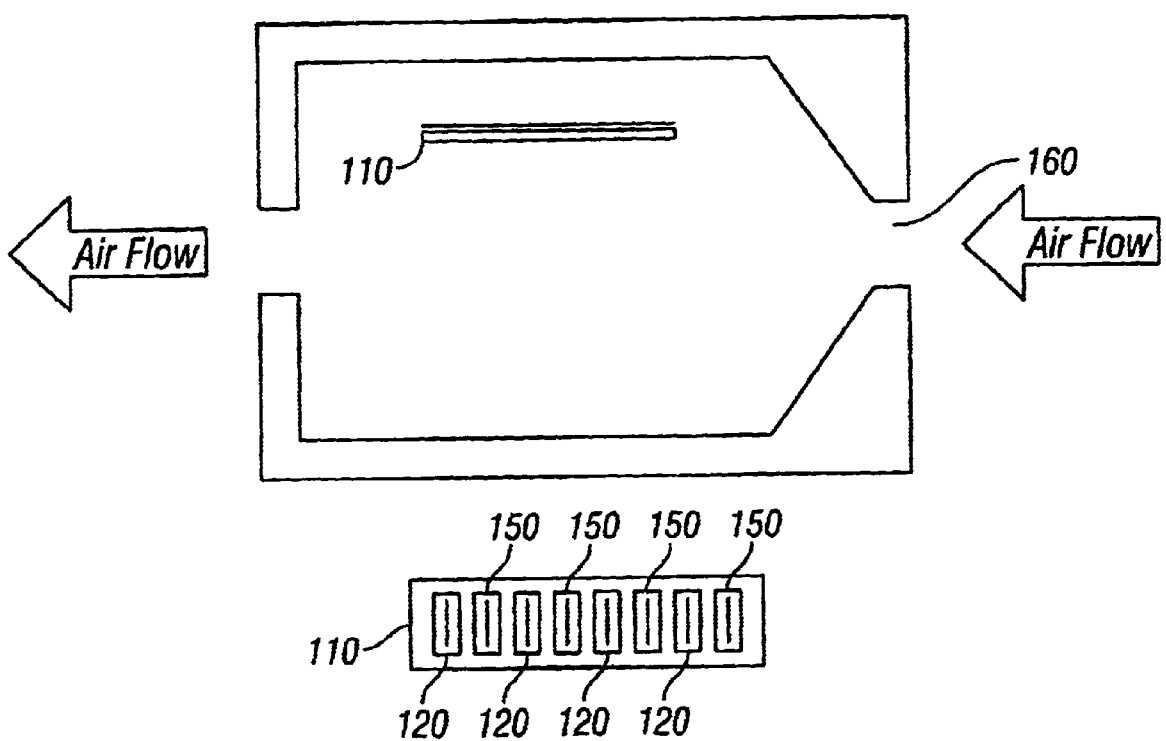
FIG. 1(B) is a block diagram depicting an alternate embodiment of sensor array 110.
Figure 3:
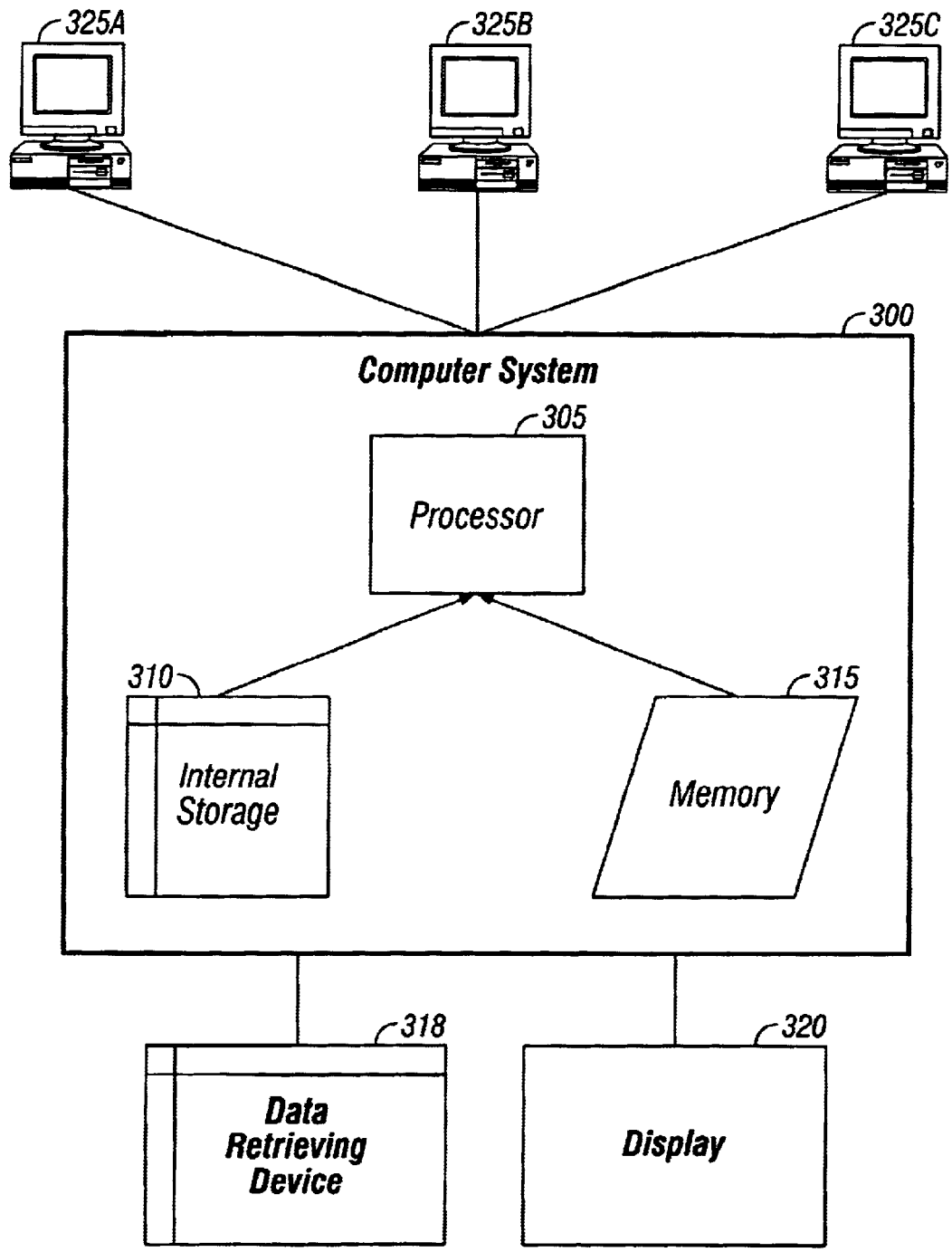
FIG. 3 is a block diagram of a general purpose computer system useful in the invention.

FIG. 1 illustrates a system 100 for detecting an analyte in a sample. System 100 includes a sensor array 110, in which an arrangement of at least one sensor 120 is present. Optionally, sensor array 110 can be configured to include a sample channel 130. A sample to be analyzed, which may be in gaseous or liquid form, is exposed to sensor array 110 through inlet 160, for example, from reservoir 170. Response signals from the sensors 120 in sensor array 110 resulting from exposure of the sample to the sensor array 110 are received and processed in detector 180, which may include, for example, signal-processing electronics, a general-purpose programmable digital computer system of conventional construction (see, for example, FIG. 3), or the like. The detector 180 can be configured to generate a digital representation of the analyte and includes a communication port or transmission device 190 coupled to the detector for communicating the digital representation of the analyte to a remote location 195 for analysis and identification of the analyte or sample.

A method 200 to remotely detect an analyte is illustrated in FIGS. 2(A–B). A sample including an analyte is introduced to a sensor array 110 (FIG. 1) which interacts with a sensor or sensors providing a detectable signal. Detector 180 detects the detectable signal (step 210) and converts the detectable signal to a digital representation or fingerprint of the detectable signal (step 220).

Figure 2A:
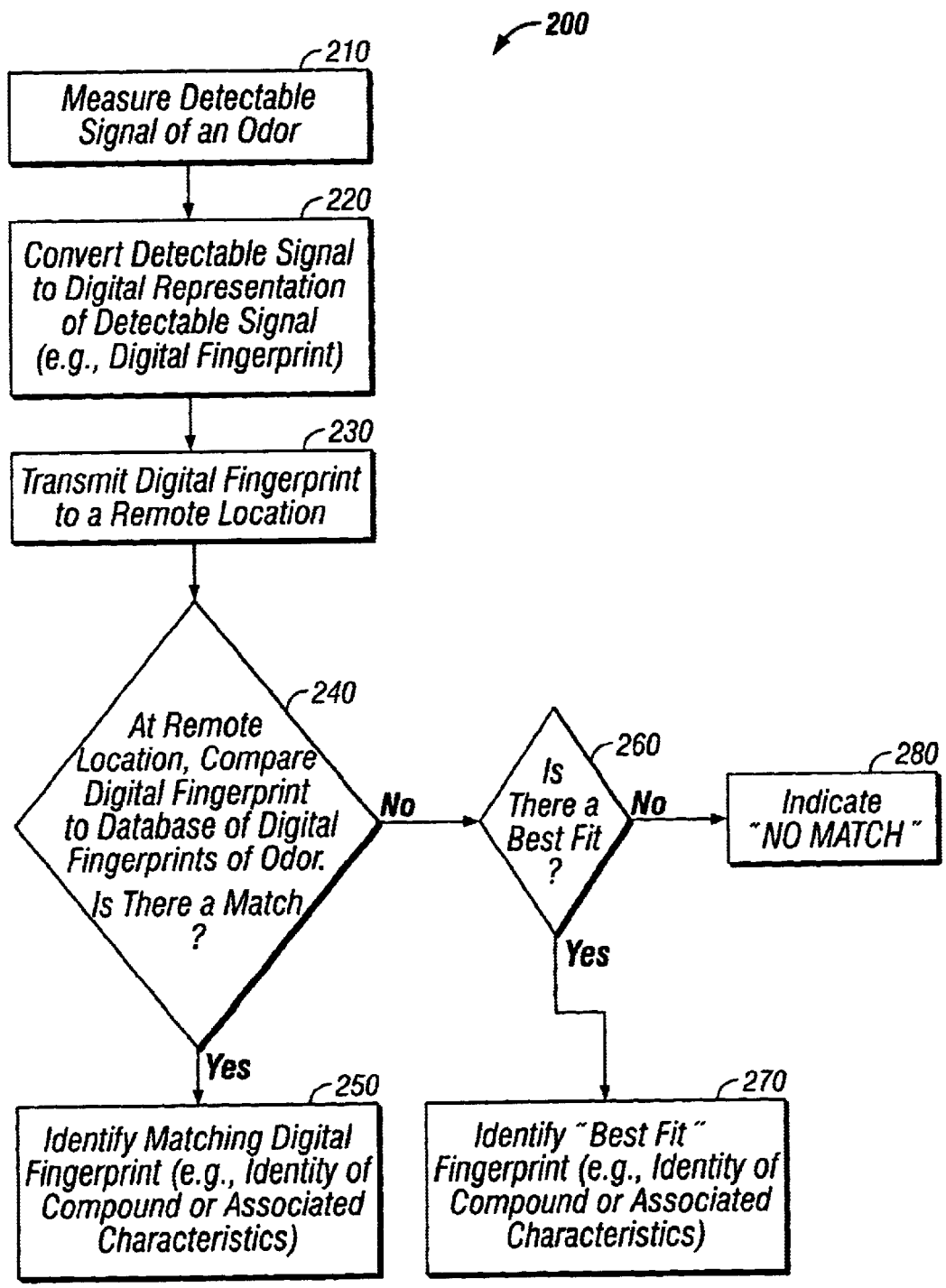
FIGS. 2A–B are flow diagrams illustrating two methods of remotely identifying an odor sample.

In the embodiment depicted in FIG. 2A, the digital signal (i.e., digital data) is transmitted to a remote location (step 230) by the transmission device 190. The digital signals (i.e., digital data) are then processed to detect and or characterize an analyte or combination of analytes in the sample by comparing the digital data to a database of digital odor fingerprints to determine if there is a match (step 240). If a match is found the matching digital fingerprint including any data related to the matching fingerprint is identified (step 250). If there is no match, the method may include a determination of a "best fit" fingerprint (step 260). "Best fit" computations are known in the art. If a "best fit" is found, the "best fit" digital fingerprint including any data related to the fingerprint is identified (step 270). If no match or "best fit" is found "No Match" is indicated (step 280).

Figure 2B:
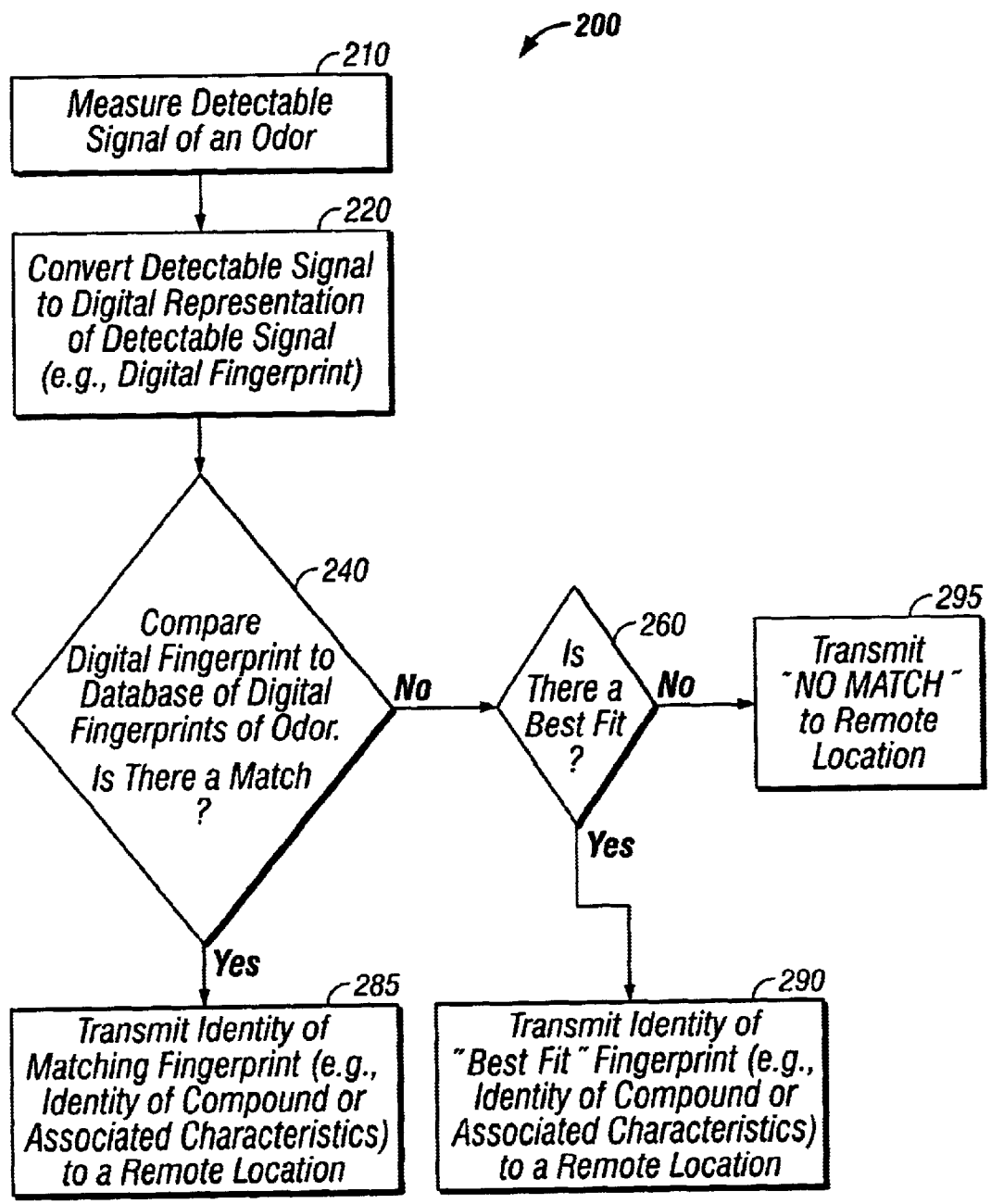

In the embodiment depicted in FIG. 2B the digital signal (i.e., digital data) is analyzed locally and the results of the analysis are transmitted remotely. For example with reference to FIG. 2B the digital signal (i.e., the digital data) is first processed to detect and or characterize an analyte or combination of analytes in the sample by comparing the digital data to a database of digital odor fingerprints to determine if there is a match (step 240). If a match is found the matching digital fingerprint including any data related to the matching fingerprint is identified and transmitted to a remote location (step 285) by transmission device 190. If there is no match, the method may include a determination of a "best fit" fingerprint (step 260). "Best fit" computations are known in the art. If a "best fit" is found, the "best fit" digital fingerprint including any data related to the fingerprint is identified and transmitted to a remote location (step 290) by transmission device 190. If no match or "best fit" is found, "No Match" is indicated and transmitted to a remote location (step 295) by transmission device 190. It is to be understood the mining of the database is included in the invention even if there is no match. Comparisons, such as those described above, can provide information regarding changes that have occurred over time with respect to analyte profiles in the environment or a subject's breath, tissue, blood or other biological sample. For example, analysis of a sample from a subject's breath can indicate that there is a change or difference between the first and one or more subsequence samples due to the loss of a particular disease indicated by the presence of a particular analyte in the sample profile.

Sensors 120 can include any of a variety of known sensors, including, for example, surface acoustic wave sensors, quartz crystal resonators, metal oxide sensors, dye-coated fiber optic sensors, dye-impregnated bead arrays, micromachined cantilever arrays, composites having regions of conducting material and regions of insulating organic material, composites having regions of conducting material and regions of conducting or semi-conducting organic material, chemically-sensitive resistor or capacitor films, metal-oxide-semiconductor field effect transistors, bulk organic conducting polymeric sensors, and other known sensor types, such as olfactory receptor proteins (ORPs) coated onto the surface of a piezoelectric (PZ) electrode (Wu, Biosens Bioelectron, 14(1):9–18, 1999).

Techniques for constructing arrays of such sensors are known, as disclosed in Harsanyi, G., Polymer Films in Sensor Applications (Technomic Publishing Co., Basel, Switzerland, 1995), and U.S. Pat. Nos. 6,017,440, 6,013,229 and 5,911,872 and co-pending U.S. patent application Ser. No. 09/409,644, filed Oct. 1, 1999, which are incorporated by reference herein. Techniques for fabricating particular sensor types are disclosed in Ballantine et al., Anal. Chem., 58:3058, 1986; Grate et al., Sens. Actuators B, 3:85, 1991; Grate et al., Anal. Chem., 65:1868, 1993; Nakamoto et al., Sens. Actuators B 1, 10:85, 1993 (surface acoustic wave (SAW) devices), Gardner et al., Sens. Actuators B, 4:117, 1991; Gardner et al., Sens. Actuators B, 6:71, 1992; Corcoran et al., Sens. Actuators B, 15:32, 1993 (tin oxide sensors), Shurmer et al., Sens. Actuators B, 4:29, 1991; Pearce et al., Analyst, 118:37, 1993, (conducting organic polymers), Freund, M. S.; Lewis, N. S. Proc. Natl. Acad. Sci, 92:2652, 1995 (materials having regions of conductors and regions of insulating organic material), White et al., Anal. Chem., 68:2191, 1996 (dye-impregnated polymer films on fiber optic sensors), Butler et al., Electrochem. Soc., 137:1325, 1990; Hughes et al., J. Biochem. and Biotechnol., 41:77, 1993 (polymer-coated micromirrors), Slater et al., J. Analyst, 119:191, 1994; Slater et al., Analyst, 116:1125, 1991 (quartz crystal microbalances (QCMs)), Keyvani et al., Sens. Actuators B, 5:199, 1991 (electrochemical gas sensors), Zubkans et al., Thin Solid Films, 268:140, 1995 (chemically sensitive field-effect transistors) and Lonergan et al., Chem. Mater., 8:2298, 1996 (carbon black-polymer composite chemiresistors). Additional sensor array fabrication techniques are disclosed in Albert, K. J., Lewis, N. S., et al., Cross-Reactive Chemical Sensor Arrays, Chemical Reviews, 2000, 100 (in press) and the references cited therein, as well as U.S. patent application Ser. No. 09/409, 644, filed Oct. 1, 1999, the disclosure of which is incorporated herein.

In one implementation, sensor array 110 incorporates multiple sensing modalities, for example comprising an arrangement of cross-reactive sensors 120 selected from known sensor types, such as those listed above, such that a given analyte elicits a response from multiple sensors in the array and each sensor responds to many analytes. In one embodiment, the sensors in the array 110 are broadly cross-reactive, meaning each sensor in the array responds to multiple analytes, and, in turn, each analyte elicits a response from multiple sensors.

By "analyte" is meant any molecule or compound. By "gaseous or vapor phase analyte" is meant a molecule or compound that is present, for example, in the headspace of a liquid, in ambient air, in a breath sample, in a gas, or as a contaminant in any of the foregoing. It will be recognized that the physical state of the gas or vapor phase can be changed by pressure, temperature as well as by affecting surface tension of a liquid by the presence of or addition of salts etc.

Detecting an analyte includes generating a response profile indicative of the presence of the analyte based on changes in a detectable signal from at least one sensor. The response profile can be derived over a period of time (e.g., continuously) due to adsorption or diffusion of the analyte into or on a particular sensor type, or may be obtained by detecting a change in the detectable signal of the sensor at a single time point or plurality of time points (e.g., t=0, t=1 sec, t—2 sec, . . . etc.). By "detectable signal" is meant a change in the sensor from a first state to a second state, which can be visually, electronically or acoustically detected. A detectable signal generated by a sensor upon adsorption by any particular analyte generates a response fingerprint corresponding to the detectable signal from at least one or more sensors. For example, a plurality of sensors allows expanded utility because the signal for an imperfect "key" for one sensor can be recognized through information gathered on another, chemically or physically dissimilar sensor in the array. A distinct pattern of responses produced over the collection of sensors in the array can provide a fingerprint that allows classification and identification of the analyte, whereas, in some instances, such information would not have been obtainable by relying on the signals arising solely from a single sensor or sensing material. The fingerprint of the analyte can include a plurality of different detectable signals and includes variations in degrees or amplitude of a detectable signal. A digital representation of the detectable signal generated by the sensor is created and communicated to a remote location for analysis.

The digital representation of the detectable signal is transmittable over any number of media. For example, such digital data can be transmitted over the Internet in encrypted or in publicly available form. The data can be transmitted over phone lines, fiber optic cables or various air-wave frequencies. The data are then analyzed by a central processing unit at a remote site, and/or archived for compilation of a data set that could be mined to determine, for example, changes with respect to historical mean "normal" values of the breathing air in confined spaces, of human breath profiles, and of a variety of other long term monitoring situations where detection of analytes in a sample is an important value-added component of the data.

A computer can be configured to characterize the analyte based on the fingerprint (e.g., the detectable signal from one or more sensors). By developing a catalogue of information on chemically diverse sensors—made, for example, with varying ratios of semi-conductive, conducting and insulating components and by differing fabrication routes—a database of analyte fingerprints can be created. The identity of the chemical analyte may or may not be known. Accordingly, an analyte fingerprint in the database can be associated with its identity or a number of other criteria, including for example, where the analyte fingerprint was obtained, the temperature, subject, disease state, location and other criteria associated with a fingerprint can be contained in the database. In addition, sensors can be chosen that are appropriate for the analytes expected in a particular application, their concentrations and the desired response times.

By profiling or fingerprinting analytes (both known and unknown) a structure-function-association database correlating analytes and fingerprints can be generated. Unknown analytes can then be characterized or identified using response pattern comparison and recognition algorithms. The present invention is not limited to any particular algorithm for comparing response fingerprints as one skilled in the art will recognize a number of ways to implement a comparison algorithm. For example, data analysis can be performed using standard chemometric methods such as principal component analysis and SIMCA, which are available in commercial software packages that run on a PC or which are easily transferred into a computer running a resident algorithm or onto a single analysis chip either integrated into, or working in conjunction with, the sensor electronics. The Fisher linear discriminant is one algorithm for analysis of the data, as described in more detail below. More sophisticated algorithms and supervised or unsupervised neural network based learning/training methods can be applied as well (Duda, R. O.; Hart, P. E. Pattern Classification and Scene Analysis; John Wiley & Sons: New York, 1973, pp. 482).

For example, in one embodiment of signal processing, the Fisher linear discriminant searches for the projection vector, w, in the detector space which maximizes the pairwise resolution factor, i.e., rf, for each set of analytes, and reports the value of rf along this optimal linear discriminant vector. The rf value is an inherent property of the data set and does not depend on whether principal component space or original detector space is used to analyze the response data. This resolution factor is basically a multi-dimensional analogue to the separation factors used to quantify the resolving power of a column in gas chromatography, and thus the rf value serves as a quantitative indication of how distinct two patterns are from each other, considering both the signals and the distribution of responses upon exposure to the analytes that comprise the solvent pair of concern. For example, assuming a Gaussian distribution relative to the mean value of the data points that are obtained from the responses of the array to any given analyte, the probabilities of correctly identifying an analyte as a or b from a single presentation when a and b are separated with resolution factors of 1.0, 2.0 or 3.0 are approximately 76%, 92% and 98% respectively.

In addition, various general purpose machines may be used with programs written in accordance with the teachings herein, or it may be more convenient to construct more specialized apparatus to perform the operations. However, preferably the embodiment is implemented in one or more computer programs executing on programmable systems each comprising at least on processor, at least one data storage system (including volatile and non-volatile memory and/or storage elements), at least one input device, and at least one output device. The program is executed on the processor to perform the functions described herein.

Each such program may be implemented in any desired computer language (including machine, assembly, high level procedural, or object oriented programming languages) to communicate with a computer system. In any case, the language may be a compiled or interpreted language. The computer program will typically be stored on a storage media or device (e.g., ROM, CD-ROM, or magnetic or optical media) readable by a general or special purpose programmable computer, for configuring and operating the computer when the storage media or device is read by the computer to perform the procedures described herein. The system may also be considered to be implemented as a computer-readable storage medium, configured with a computer program, where the storage medium so configured causes a computer to operate in a specific and predefined manner to perform the functions described herein.

Embodiments of the invention include systems (e.g., internet based systems), particularly computer systems which store and manipulate the data corresponding to the detectable signal obtained from an analyte, described herein. One example of a computer system 100 is illustrated in block diagram form in FIG. 3. As used herein, "a computer system" refers to the hardware components, software components, and data storage components used to analyze the digital information obtained from odor sensors. The computer system 100 typically includes a processor for processing, accessing and manipulating the data. The processor 105 can be any well-known type of central processing unit, such as, for example, the Pentium III from Intel Corporation, or similar processor from Sun, Motorola, Compaq, AMD or International Business Machines.

Typically the computer system 300 is a general purpose system that comprises the processor 305 and one or more internal data storage components 310 for storing data, and one or more data retrieving devices for retrieving the data stored on the data storage components. A skilled artisan can readily appreciate that any one of the currently available computer systems are suitable.

In one particular embodiment, the computer system 300 includes a processor 305 connected to a bus which is connected to a main memory 315 (preferably implemented as RAM) and one or more internal data storage devices 310, such as a hard drive and/or other computer readable media having data recorded thereon. In some embodiments, the computer system 300 further includes one or more data retrieving device 318 for reading the data stored on the internal data storage devices 310.

The data retrieving device 318 may represent, for example, a floppy disk drive, a compact disk drive, a magnetic tape drive, or a modem capable of connection to a remote data storage system (e.g., via the internet) and the like. In some embodiments, the internal data storage device 310 is a removable computer readable medium such as a floppy disk, a compact disk, a magnetic tape, and the like, containing control logic and/or data recorded thereon. The computer system 300 may advantageously include or be programmed by appropriate software for reading the control logic and/or the data from the data storage component once inserted in the data retrieving device.

Accordingly, a remote analyte detection system of the invention includes at least one sensor and may include a plurality of sensors, a measuring device for detecting a signal at the sensor(s), a device for transmitting the signal data to a remote location, a computer, a data structure of sensor response profiles or fingerprints, and a comparison algorithm. The measuring device is adapted for the type of sensor used (e.g., electrical measuring devices for resistor based sensors and acoustic based devices for vibrational or sound based sensors). In one embodiment, the electrical measuring device is an integrated circuit comprising neural network-based hardware and a digital-analog converter (DAC) multiplexed to each sensor, or a plurality of DACs, each connected different sensor(s).

Embodiments of the invention include remote systems for vapor or odor phase detection of an analyte. The system can be associated with robotic devices that can enter hazardous areas to detect explosives, weaponry, mines, and hazardous chemicals. In one embodiment, the robotic device can enter disaster areas (e.g., collapsed buildings) to locate hazardous chemicals or trapped persons, for example. The system can assist in detecting injuries associated with such trapped persons by obtaining, for example, breath samples (as discussed more fully below). In another embodiment, the systems can be used in space or on other planets to detect chemicals, air content and the like. The designing of a specific robotic system is well within the ability of one skilled in the art. For example, in view of the teaching herein, a person skilled in the art, can easily design a robotic system incorporating the sensors of the invention.

Twenty to thirty different sensors are typically sufficient for many analyte classification tasks but larger array sizes can be implemented as well. Temperature and humidity can be controlled but because a preferred mode is to record changes relative to the ambient baseline condition, and because the patterns for a particular type and concentration of odorant are generally independent of such baseline conditions, it is not critical to actively control these variables in some implementations of the technology. Such control could be achieved either in open-loop or closed-loop configurations.

The sensors and sensor arrays disclosed herein could be used with or without preconcentration of the analyte depending on the power levels and other system constraints demanded by the user. Regardless of the sampling mode, the characteristic patterns (both from amplitude and temporal features, depending on the most robust classification algorithm for the purpose) associated with certain disease states and other volatile analyte signatures can be identified using the sensors disclosed herein. These patterns are then stored in a library, and matched against the signatures emanating from the sample to determine the likelihood of a particular odor falling into the category of concern (disease or nondisease, toxic or nontoxic chemical, good or bad polymer samples, fresh or old fish, fresh or contaminated air, and the like.).

Analyte sampling will occur differently in the various application scenarios. For some applications, direct headspace samples can be collected using either single breath and urine samples in the case of sampling a patient's breath for the purpose of disease or health state differentiation and classification. In addition, extended breath samples, passed over a Tenax, Carbopack, Poropak, Carbosieve, or other sorbent preconcentrator material, can be obtained when needed to obtain robust intensity signals. The absorbent material of the fluid concentrator can be, but is not limited to, a nanoporous material, a microporous material, a chemically reactive material, a nonporous material and combinations thereof. In certain instances, the absorbent material can concentrate the analyte by a factor that exceeds a factor of about $10^5$, or by a factor of about $10^2$ to about $10^4$. In another embodiment, removal of background water vapor is conducted in conjunction, such as concomitantly, with the concentration of the analyte. Once the analyte is concentrated, it can be desorbed using a variety of techniques, such as heating, purging, stripping, pressuring or a combination thereof.

Breath samples can be collected through a straw or suitable tube in a patient's mouth that is connected to the sample chamber (or preconcentrator chamber), with the analyte outlet available for capture to enable subsequent GC/MS or other selected laboratory analytical studies of the sample. In other applications, headspace samples of odorous specimens can be analyzed and/or carrier gases can be used to transmit the analyte of concern to the sensors to produce the desired response. In still other cases, the analyte will be in a liquid phase and the liquid phase will be directly exposed to the sensors; in other cases the analyte will undergo some separation initially and in yet other cases only the headspace of the analyte will be exposed to the sensors.

Using the devices of the invention, the analyte can be concentrated from an initial sample volume of about 10 liters and then desorbed into a concentrated volume of about 10 milliliters or less, before being presented to a sensor or sensor array.

Suitable commercially available adsorbent materials include but are not limited to, Tenax TA, Tenax GR, Carbotrap, Carbopack B and C, Carbotrap C, Carboxen, Carbosieve SIII, Porapak, Spherocarb, and combinations thereof. Preferred adsorbent combinations include, but are not limited to, Tenax GR and Carbopack B; Carbopack B and Carbosieve SIII; and Carbopack C and Carbopack B and Carbosieve SIII or Carboxen 1000. Those skilled in the art will know of other suitable absorbent materials.

In another embodiment, removal of background water vapor is conducted in conjunction, such as concomitantly, with the concentration of the analyte. Once the analyte is concentrated, it can be desorbed using a variety of techniques, such as heating, purging, stripping, pressuring or a combination thereof. In these embodiments, the sample concentrator is typically wrapped with a wire through which current can be applied to heat and thus, desorb the concentrated analyte. The analyte is thereafter transferred to the sensor array.

In some cases, the array will not yield a distinct signature of each individual analyte in a region, unless one specific type of analyte dominates the chemical composition of a sample. Instead, a pattern that is a composite, with certain characteristic temporal features of the sensor responses that aid in formulating a unique relationship between the detected analyte contents and the resulting array response, will be obtained.

The sensors and sensor arrays disclosed herein act as an "electronic nose" to offer ease of use, speed, and identification of analytes and/or analyte regions all in a portable, relatively inexpensive implementation. Thus, a "sample" includes a wide variety of analytes and fluids which can be analyzed by the disclosed sensors, arrays and noses so long as the subject analyte is capable generating a differential response across a plurality of sensors of the array. For example, a sample can be an environmental sample and includes atmospheric air, ambient air, water, sludge, and soil to name a few. In addition, a sample can be a biological sample, including, for example, a subject's breath, saliva, blood, urine, feces, and various tissues to name a few.

Analyte applications include broad ranges of chemical classes such as organics including, for example, alkanes, alkenes, alkynes, dienes, alicyclic hydrocarbons, arenes, alcohols, ethers, ketones, aldehydes, carbonyls, carbanions, biogenic amines, thiols, polynuclear aromatics and derivatives of such organics, e.g., halide derivatives, etc., biomolecules such as sugars, isoprenes and isoprenoids, fatty acids and derivatives, etc. Accordingly, commercial applications of the sensors, arrays and noses include environmental toxicology and remediation, biomedicine, materials quality control, food and agricultural products monitoring, anaesthetic detection, automobile oil or radiator fluid monitoring, breath alcohol analyzers, hazardous spill identification, explosives detection, fugitive emission identification, medical diagnostics, fish freshness, detection and classification of bacteria and microorganisms both in vitro and in vivo for biomedical uses and medical diagnostic uses, monitoring heavy industrial manufacturing, ambient air monitoring, worker protection, emissions control, product quality testing, leak detection and identification, oil/gas petrochemical applications, combustible gas detection, $H_2S$ monitoring, hazardous leak detection and identification, emergency response and law enforcement applications, illegal substance detection and identification, arson investigation, enclosed space surveying, utility and power applications, emissions monitoring, transformer fault detection, food/beverage/agriculture applications, freshness detection, fruit ripening control, fermentation process monitoring and control applications, flavor composition and identification, product quality and identification, refrigerant and fumigant detection, cosmetic/perfume/fragrance formulation, product quality testing, personal identification, chemical/plastics/pharmaceutical applications, leak detection, solvent recovery effectiveness, perimeter monitoring, product quality testing, hazardous waste site applications, fugitive emission detection and identification, leak detection and identification, perimeter monitoring, transportation, hazardous spill monitoring, refueling operations, shipping container inspection, diesel/gasoline/aviation fuel identification, building/residential natural gas detection, formaldehyde detection, smoke detection, fire detection, automatic ventilation control applications (cooking, smoking, etc.), air intake monitoring, hospital/medical anesthesia & sterilization gas detection, infectious disease detection and breath applications, body fluids analysis, pharmaceutical applications, drug discovery, telesurgery, and the like. Another application for the sensor-based fluid detection device in engine fluids is an oil/antifreeze monitor, engine diagnostics for air/fuel optimization, diesel fuel quality, volatile organic carbon measurement (VOC), fugitive gases in refineries, food quality, halitosis, soil and water contaminants, air quality monitoring, leak detection, fire safety, chemical weapons identification, use by hazardous material teams, explosive detection, breathalyzers, ethylene oxide detectors and anaesthetics.

Biogenic amines such as putrescine, cadaverine, and spermine are formed and degraded as a result of normal metabolic activity in plants, animals and microorganisms and can be identified in order to assess the freshness of foodstuffs such as meats (Veciananogues, J. Agr. Food Chem., 45:2036–2041, 1997), cheeses, alcoholic beverages, and other fermented foods. Additionally, aniline and o-toluidine have been reported to be biomarkers for subjects having lung cancer (Preti et al., J. Chromat. Biomed. Appl. 432:1–11, 1988), breath ammonia in diagnosis, treatment assessment, and follow-up in hepatic encephalopathy (Shimamoto et al., Hepatogastroenterology, 47(32):443–5, 2000), while dimethylamine and trimethylamine have been reported to be the cause of the "fishy" uremic breath odor experienced by patients with renal failure.(Simenhoff, New England J. Med., 297:132–135, 1977). Thus, in general biogenic amines and thiols are biomarkers of bacteria, disease states, food freshness, and other odor-based conditions. Thus, the electronic nose sensor elements and arrays discussed herein can be used to monitor the components in the headspace of urine, blood, sweat, and saliva of human patients, as well as breath, to diagnose various states of health, such as the timing of estrus (Lane et al., J Dairy Sci 81(8):2145–50, 1998), and diseases as discussed herein. In addition, they can be used for food quality monitoring, such as fish freshness (which involves volatile amine signatures), for environmental and industrial applications (oil quality, water quality, air quality and contamination and leak detection), for other biomedical applications, for law enforcement applications (breathalayzers), for confined space monitoring (indoor air quality, filter breakthrough, etc.) and for other applications delineated above to add functionality and performance to sensor arrays through improvement in analyte detection by use in arrays that combine sensor modalities. Accordingly, the invention provides physicians and patients with a method to monitor illness and disease from remote locations. It is envisioned that the systems of the invention will be useful in medical care personnel monitoring patients who are bed-ridden at home or whom require continual monitoring of a particular disease state. Such remote monitoring ability eliminates the need for repeated trips to a doctors office or hospital and can provide physicians with real-time data regarding a patient's health and well-being.

For example, breath testing has long been recognized as a nonintrusive medical technique that allows for the diagnosis of disease by linking specific volatile organic vapor metabolites in exhaled breath to medical conditions (see Table 1). In addition to breath analysis being nonintrusive, it offers several other potential advantages in certain instances, such as 1) breath samples are easy to obtain, 2) breath is in general a much less complicated mixture of components than either serum or urine samples, 3) direct information can be obtained on the respiratory function that is not readily obtainable by other means, 4) breath analysis offers the potential for direct real time monitoring of the decay of toxic volatile substances in the body, and 5) breath analysis can be performed at remote locations (e.g., away from a physician's office). Table 1 lists some of the volatile organic analytes that have been identified as targets for specific diseases using gas chromatography/mass spectrometry (GC/MS) methods, with emphasis on amines.

TABLE 1

| Patient Diagnosis | Target VOCs | VOC Source |
|---|---|---|
| Uremia; Preti, 1992; Simenhoff, 1977; Davies, 1997 | dimethylamine, trimethylamine | breath, urine |
| Trimethylaminuria; Preti, 1992; Alwaiz, 1989 | trimethylamine | breath, urine, sweat, vaginal discharge |
| Lung Cancer; Preti, 1992 | aniline, o-toluidine | lung air |
| Dysgeusia/Dysosmia; Preti, 1992; Oneill, 1988 | hydrogen sulfide, methyl mercaptn, pyridine, aniline, diphenylamine, dodecanol | lung air |
| Cystinuria; Manolis A., 1983, Clin. Chem. 29:5. | cadaverie, piperidine, putrescine, pyrrolidine | breath |
| Halitosis; Kozlovsky, 1994; Preti. 1992 | hydrogen sulfide, methyl mercaptan, cadaverine, putrescine, indole, skatole | mouth air |
| Bacterial Vaginosis; Chandiok, 1997, J. Clinical Path., 50:790. | amines | vaginal cavity and discharge |
| Liver cirrhosis Shimamoto Hepatogastroenterology 2000 Mar–Apr; 47 (32): 443–5 | ammonia | blood; breath |

In one embodiment, the invention is used with subjects who potentially have a medical condition such as, for example, diabetes mellitus or any disease having a by-product chemical analyte as described in Table 1, to improve diagnosis and treatment of medical disorder more accurate and to assist medical practitioners in determining the proper amount of medication or other treatment to prescribe. The term medical practitioner is intended to include any individual who treats, or prescribes treatment to another individual to improve the latter's health or well-being. The focus of this invention is to gather, organize, and present data which is collected at a location away from a medical practitioner's office. The data may be collected over a long period of time in a way that best facilitates accurate diagnosis and proper treatment of such medical conditions which require long-term profiling of medical readings.

In one embodiment, data is gathered, transmitted, stored, and available to the medical practitioner at their convenience. The data are gathered using a sensor system as described herein. For example, a sensor system of the invention adapted, for example, with a straw to collect a breath sample can be used. Once the data are gathered, it is stored and transmitted or simultaneously transmitted to a remote site. At the remote site the data can be added to a database for storage, such that it is available for use when required by a medical practitioner. Alternatively, the information could be stored in a network server in a common LAN or fiber optic network if available, e.g. in hospitals and HMOs, which often have their own dedicated computer networks to connect their administrative offices, laboratories, and doctor offices, and on which their patient medical records are stored. In the case of private practices, the Internet could be used, with adequate security precautions taken to prevent unauthorized access to the information, or the information could be uploaded directly to a computer system acting as a database server via modem-to-modem communication over telephone lines.

By virtue of the foregoing method(s), medical practitioners' needs relating to hard-to-identify chronic medical conditions and medical conditions which can depend on long-term profiling for proper treatment are effectively met.

The sensor system of the invention is described herein with reference to resistive sensors, however, other types of sensors are applicable to the invention including, for example, heated metal oxide thin film resistors, polymer sorption layers on the surfaces of acoustic wave resonators, arrays of electrochemical detectors, conductive polymers or composites that consist of regions of conductors and regions of insulating organic materials, quartz crystal microbalance arrays, and the like described herein.

A sensor and sensor array comprises a plurality of differently responding chemical sensors. In one embodiment, the array has at least one sensor comprising at least a first and second conductive lead electrically coupled to and separated by a chemically sensitive resistor. The leads may be any convenient conductive material, usually a metal, and may be interdigitized to maximize signal-to-noise strength.

In a sensor array of the invention one or more sensors are coupled individually or as groups to an applicable detector for detecting signal changes in the sensor. For example, in one embodiment, the array is comprised of one or more sensors having regions of an electrical conductor (e.g., an organic electrical conductor) with regions of a compositionally dissimilar material that is an electrical conductor or a non-conductive material. The conductive sensor forms a resistor comprising a plurality of alternating regions of differing compositions and therefore differing conductivity transverse to the electrical path between the conductive leads. Generally, a sensor is fabricated by blending a conductive material with a conductive organic material, insulator, non-conductive organic polymer, blends or co-polymers. For example, in a colloid, suspension or dispersion of particulate conductive material in a region of conductive organic material, insulator, non-conductive organic polymer, blends or co-polymers, the regions separating the particles provide changes in conductance relative to the conductance of the particles themselves. The gaps of different conductance arising from the conductive material range in path length from about 10 to 1,000 angstroms, usually on the order of 100 angstroms. The path length and resistance of a given gap is not constant but rather changes as the material absorbs, adsorbs or imbibes an analyte. Accordingly the dynamic aggregate resistance provided by these gaps in a given resistor is a function of analyte permeation of the conductive organic regions of the material. In some embodiments, the conductive material may also contribute to the dynamic aggregate resistance as a function of analyte permeation (e.g., when the conductive material is a conductive organic polymer such as polypyrrole and is blended with another organic conducting material to form the composite).

A wide variety of conductive materials and dissimilar materials can be used. In one embodiment, one such region is comprised of an inorganic (Au, Ag) or organic (carbon black) conductive material, while the other region is comprised of a compositionally dissimilar organic conducting polymer (polyaniline, polypyrrole, polythiophene, polyEDOT, and other conducting organic polymers such as those in the Handbook of Conducting Polymers (Handbook of Conducting Polymers, second ed., Marcel Dekker, New York 1997, vols. 1 & 2)). Other combinations of conductor/organic conductor/composite materials are also useful.

In one implementation, an electrically conductive material that is dopable or undopable by protons can be used as the organic material in a composite where the compositionally different conductor is carbon black.

In another implementation, polyaniline is a desirable member in the class of conducting polymers in that the half oxidized form, the emeraldine base (y=0.5), is rendered electrically conductive upon incorporation of a strong acid. The conductive form of polyaniline, commonly referred to as the emeraldine salt (ES), has been reported to deprotonate to the emeraldine base and become insulating in alkaline environments.

Table 2 provides exemplary conductive materials for use in sensor fabrication; blends, such as of those listed, may also be used. Typically conductors include, for example, those having a positive temperature coefficient of resistance. The sensors are comprised of a plurality of alternating regions of a conductor with regions of a compositionally dissimilar conducting organic material. Without being bound to any particular theory, it is believed that the electrical pathway that an electrical charge traverses between the two contacting electrodes traverses both the regions of the conductor and the regions of the organic material.

TABLE 2

| Major | Class Examples |
| --- | --- |
| Organic Conductors conducting polymers | poly(anilines), poly(thiophenes, poly(pyrroles), poly(aceylenes, etc.)), carbonaceous material (carbon blacks, graphite, coke, C60 etc.), charge transfer complexes (tetramethylparaphenylenediamine-chloranile, alkali metal tetracyanoquinodimethane complexes, tetrathiofulvalene halide complexes, etc.), etc. |

TABLE 2-continued

| Major | Class Examples |
| --- | --- |
| Inorganic Conductors metals/metal alloys | Ag, Au, Cu, Pt, AuCu alloy, etc.), highly doped semiconductors (Si, GaAs, InP, $MoS_2$, $TiO_2$, etc.), conductive metal oxides ($In_2O_3$, $SnO_2$, $Na_2Pt_3O_4$, etc.), superconductors ($Yba_2Cu_3O_7$, $Ti_2Ba_2Ca_2Cu_3O_{10}$, etc.), etc. |
| Mixed inorganic/organic Conductor | Tetracyanoplatinate complexes, Iridium halocarbonyl complexes, stacked macrocyclic complexes. Etc. |

In one embodiment, the conducting region can be anything that can carry electrons from atom to atom, including, but not limited to, a metal, a polymer, a substrate, an ion, an alloy, an organic material, (e.g., carbon, graphite, etc.) an inorganic material, and a biomaterial.

In certain other embodiments, the conductive material is a conductive particle, such as a colloidal nanoparticle. As used herein the term "nanoparticle" refers to a conductive cluster, such as a metal cluster, having a diameter on the nanometer scale. Such nanoparticles are optionally stabilized with organic ligands.

Examples of colloidal nanoparticles for use in accordance with the invention are described in the literature. In this embodiment, the electrically conductive organic region can optionally be a ligand that is attached to a central core making up the nanoparticle. These ligands i.e., caps, can be polyhomo- or polyhetero-functionalized, thereby being suitable for detecting a variety of chemical analytes. The nanoparticles, i.e., clusters, are stabilized by the attached ligands. In certain embodiments, the conducting component of the resistors are nanoparticles comprising a central core conducting element and an attached ligand optionally in a polymer matrix. With reference to Table 2, various conducting materials are suitable for the central core. In certain embodiments, the nanoparticles have a metal core. Typical metal cores include, but are not limited to, Au, Ag, Pt, Pd, Cu, Ni, AuCu and regions thereof. Gold (Au) is most typical. These metallic nanoparticles can be synthesized using a variety of methods. In a one method of synthesis, a modification of the protocol developed by Brust et al. can be used. (see, Brust et al., J. Chem. Soc., Chem. Commun., 801–802, 1994.) As explained more fully below, by varying the concentration of the synthetic reagents, the particle size can be manipulated and controlled.

The conductive organic material can be either an organic semiconductor or organic conductor. "Semi-conductors" as used herein, include materials whose electrical conductivity increases as the temperature increases, whereas conductors are materials whose electrical conductivity decreases as the temperature increases. By this fundamental definition, the organic materials that are useful in one embodiment of the invention are either semiconductors or conductors. Such materials are collectively referred to herein as electrically conducting organic materials because they produce a readily-measured resistance between two conducting leads separated by about 10 micron or more using readily-purchased multimeters having resistance measurement limits of 100 Mohm or less, and thus allow the passage of electrical current through them when used as elements in an electronic circuit at room temperature. Semi-conductors and conductors can be differentiated from insulators by their different room temperature electrical conductivity values.

Insulator show very low room temperature conductivity values, typically less than about $10^{-8}$ ohm$^{-1}$cm$^{-1}$. Poly (styrene), poly(ethylene), and other polymers provide examples of insulating organic materials. Metals have very high room temperature conductivities, typically greater than about 10 ohm$^{-1}$ cm$^{-1}$. Semi-conductors have conductivities greater than those of insulators, and are distinguished from metals by their different temperature dependence of conductivity, as described above. The organic materials that are useful in one embodiment of sensors are either electrical semiconductors or conductors, and have room temperature electrical conductivities of greater than about $10^{-6}$ ohm$^{-1}$ cm$^{-1}$, typically having a conductivity of greater than about $10^{-3}$ ohm$^{-1}$ cm$^{-1}$.

Accordingly, in one embodiment the sensors of the invention include sensors comprising regions of an electrical conductor and regions of a compositionally different organic material that is an electrical conductor or semiconductor. As used above, electrical conductors include, for example, Au, Ag, Pt and carbon black, other conductive materials having similar resistivity profiles are easily identified in the art (see, for example the latest edition of: The CRC Handbook of Chemistry and Physics, CRC Press, the disclosure of which is incorporated herein by reference). Furthermore, insulators can also be incorporated into the composite either in place of—or in addition to—the regions of compositionally different material, as described above, to further manipulate the analyte response properties of the composites. The insulating region (i.e., non-conductive region) can be anything that can impede electron flow from atom to atom, including, but not limited to, a polymer, a plasticizer, an organic material, an organic polymer, a filler, a ligand, an inorganic material, a biomaterial, and combinations thereof Table 3 provides examples of insulating or non-conducting organic materials that can be used for such purposes.

TABLE 3

| Major Class | Examples |
| --- | --- |
| Main-chain carbon polymers | poly(dienes), poly(alkenes), poly(acrylics), poly(methacrylics), poly(vinyl ethers), poly(vinyl thioethers), poly(vinyl alcohols), poly(vinyl ketones), poly(vinyl halides), poly(vinyl nitrites), poly(vinyl esters), poly(styrenes), poly(aryines), etc. |
| Main-chain acyclic heteroatom polymers | poly(oxides), poly(caronates), poly(esters), poly(anhydrides), poly(urethanes), poly(sulfonate), poly(siloxanes), poly(sulfides), poly(thioesters), poly(sulfones), poly(sulfonamindes), poly(amides), poly(ureas), poly(phosphazens), poly(silanes), poly(silazanes), etc. |
| Main-chain heterocyclic polymers | poly(furantetracarboxylic acid diimides), poly(benzoxazoles), poly(oxadiazoles), poly(benzothiazinophenothiazines), poly(benzothiazoles), poly(pyrazinoquinoxalines), poly(pyromenitimides), poly(quinoxalines), poly(benzimidazoles), poly(oxidoles), poly(oxoisinodolines), poly(diaxoisoindoines), poly(triazines), poly(pyridzaines), poly(pioeraziness), poly(pyridinees), poly(pioeridiens), poly(triazoles), poly(pyrazoles), poly(pyrrolidines), poly(carboranes), poly(oxabicyclononanes), |

TABLE 3-continued

| Major Class | Examples |
| --- | --- |
| | poly(diabenzofurans), poly(phthalides), poly(acetals), poly(anhydrides), carbohydrates, etc. |

Non-conductive organic polymer materials; blends and copolymers; plasticized polymers; and other variations including those using the polymers listed here, may also be used. Combinations, concentrations, blend stoichiometries, percolation thresholds, etc. are readily determined empirically by fabricating and screening prototype resistors (chemiresistors) as described below.

In another embodiment, the sensor comprises a plurality of alternating nonconductive and conductive regions transverse to an electrical path between conductive leads. Generally, these sensors are fabricated by blending a conductive material with a nonconductive organic polymer such that the electrically conductive path between the leads coupled to the sensor is interrupted by gaps of non-conductive organic polymer material. For example, in a colloid, suspension or dispersion of particulate conductive material in a matrix of nonconductive organic polymer material, the matrix regions separating the particles provide the gaps. The nonconductive gaps range in path length from about 10 to 1,000 angstroms, usually on the order of 100 angstroms providing individual resistance of about 10 to 1,000 m$\Omega$, usually on the order of 100 m$\Omega$, across each gap. The path length and resistance of a given gap is not constant but rather is believed to change as the nonconductive organic polymer of the region absorbs, adsorbs or imbibes an analyte. Accordingly the dynamic aggregate resistance provided by these gaps in a given sensor is a function of analyte permeation of the nonconductive regions. In some embodiments, the conductive material may also contribute to the dynamic aggregate resistance as a function of analyte permeation (e.g. when the conductive material is a conductive organic polymer such as polyprryole). A wide variety of conductive materials and nonconductive organic polymer materials can be used as described herein and in U.S. Pat. No. 5,571,401, which is incorporated herein by reference in its entirety.

The chemiresistors can be fabricated by many techniques such as, but not limited to, solution casting, suspension casting, and mechanical mixing. In general, solution cast routes are advantageous because they provide homogeneous structures and ease of processing. With solution cast routes, sensor elements may be easily fabricated by spin, spray or dip coating. Suspension casting still provides the possibility of spin, spray or dip coating but more heterogeneous structures than with solution casting are expected. With mechanical mixing, there are no solubility restrictions since it involves only the physical mixing of the resistor components, but device fabrication is more difficult since spin, spray and dip coating are no longer possible. A more detailed discussion of each of these follows.

For systems where both the conducting, compositionally dissimilar organic conducting and/or non-conducting material or their reaction precursors are soluble in a common solvent, the chemiresistors can be fabricated by solution casting. The oxidation of pyrrole by phosphomolybdic acid represents such a system. In this reaction, the phosphomolybdic acid and pyrrole are dissolved in tetrahydrofuran (THF) and polymerization occurs upon solvent evaporation.

This allows for THF soluble compositionally different conductive, semiconductive, and non-conductive materials to be dissolved into this reaction region thereby allowing the composite to be formed in a single step upon solvent evaporation.

A variety of permutations on this scheme are possible for other conducting polymers. Some of these are listed below. Certain conducting organic polymers, such as substituted poly(cyclooctatetraenes), are soluble in their undoped, non-conducting state in solvents such as THF or acetonitrile. Consequently, the blends between the undoped polymer and other organic materials can be formed from solution casting. After which, the doping procedure (exposure to $I_2$ vapor, for instance) can be performed on the blend to render the substituted poly(cyclooctatetraene) conductive. Again, the choice of compositionally different organic materials is limited to those that are soluble in the solvents that the undoped conducting polymer is soluble in and to those stable to the doping reaction.

Certain conducting organic polymers can also be synthesized via a soluble precursor polymer. In these cases, blends between the precursor polymer and the compositionally different material of the composite can first be formed followed by chemical reaction to convert the precursor polymer into the desired conducting polymer. For instance poly(p-phenylene vinylene) can be synthesized through a soluble sulfonium precursor. Blends between this sulfonium precursor and a non-conductive or conductive polymer can be formed by solution casting. After which, the blend can be subjected to thermal treatment under vacuum to convert the sulfonium precursor to the desired poly(p-phenylene vinylene).

In suspension casting, one or more of the components of the sensor is suspended and the others dissolved in a common solvent. Suspension casting is a rather general technique applicable to a wide range of species, such as carbon blacks or colloidal metals, which can be suspended in solvents by vigorous mixing or sonication. In one application of suspension casting, the conductive organic or conductive polymer is dissolved in an appropriate solvent (such as THF, acetonitrile, water, and the like). Carbon black is then suspended in this solution and the resulting region is used to dip coat or spray coat electrodes.

Mechanical mixing is suitable for all of the conductive/ conductive organic/non-conductive combinations possible. In this technique, the materials are physically mixed in a ball-mill or other mixing device. For instance, carbon black/ conducting organic polymer composites are readily made by ball-milling. When the semi-conductive or conductive or insulating organic material can be melted or significantly softened without decomposition, mechanical mixing at elevated temperature can improve the mixing process. Alternatively, composite fabrication can sometimes be improved by several sequential heat and mix steps.

Once fabricated, the individual sensors can be optimized for a particular application by varying their chemical make up and morphologies. The chemical nature of the sensors determines to which analytes they will respond and their ability to distinguish different analytes. The relative ratio of conductive to compositionally different organic material, along with the composition of any other insulating organic or inorganic components, can determine the magnitude of the response since the resistance of the elements becomes more sensitive to sorbed molecules as the percolation threshold is approached and as the molecules interact chemically with the components of the composite that adsorb or absorb the analyte. The film morphology is also important in determining response characteristics. For instance, uniform thin films respond more quickly to analytes than do uniform thick ones. However, it may be advantageous to include sensors of varying thickness to determine various diffusion coefficients or other physical characteristics of the analyte being analyzed. Hence, with an empirical catalogue of information on chemically diverse sensors made with varying ratios of semi-conductive, conducting, and insulating components and by differing fabrication routes, sensors can be chosen that are appropriate for the analytes expected in a particular application, their concentrations, and the desired response times. Further optimization can then be performed in an iterative fashion as feedback on the performance of an array under particular conditions becomes available.

The resistor may itself form a substrate for attaching the lead or the resistor. For example, the structural rigidity of the resistors may be enhanced through a variety of techniques: chemical or radiation cross-linking of polymer components (dicumyl peroxide radical cross-linking, UV-radiation cross-linking of poly(olefins), sulfur cross-linking of rubbers, e-beam cross-linking of Nylon, etc.), the incorporation of polymers or other materials into the resistors to enhance physical properties (for instance, the incorporation of a high molecular weight, high melting temperature ($T_m$) polymers), the incorporation of the resistor elements into supporting matrices such as clays or polymer networks (forming the resistor blends within poly(methylmethacrylate) networks or within the lamellae of montmorillonite, for instance), etc. In another embodiment, the resistor is deposited as a surface layer on a solid matrix which provides means for supporting the leads.

Sensor arrays particularly well-suited to scaled up production are fabricated using integrated circuit (IC) design technologies. For example, the chemiresistors can easily be integrated onto the front end of a simple amplifier interfaced to an A/D converter to efficiently feed or transmit the data stream directly into a neural network software or hardware analysis section at a remote location. Micro-fabrication techniques can integrate the chemiresistors directly onto a micro-chip which contains the circuitry for analog signal conditioning/processing and then data analysis. This provides for the production of millions of incrementally different sensor elements in a single manufacturing step using ink-jet technology. Controlled compositional gradients in the chemiresistor elements of a sensor array can be induced in a method analogous to how a color ink-jet printer deposits and mixes multiple colors. However, in this case rather than multiple colors, a plurality of different organic materials and conducting components suspended or dissolved in solution which can be deposited are used. A sensor array of a million distinct elements only requires a 1 cm×1 cm sized chip employing lithography at the 10 micrometer feature level, which is within the capacity of conventional commercial processing and deposition methods. This technology permits the production of sensitive, small-sized, stand-alone chemical sensors.

In one embodiment, the sensor arrays have a predetermined inter-sensor variation in the structure or composition of the organic materials as well as in the conductive components and any insulating or plasticizing components of the composites. The variation may be quantitative and/or qualitative. For example, the concentration of the organic material in the composite can be varied across sensors. Alternatively, a variety of different organic materials may be used in different sensors. The anions that accompany conducting or semi-conducting organic polymers such as polyaniline in some doping states can be compositionally varied to add diversity to the array, as can the polymer composition itself, either structurally (through use of a different family of materials) or through modification of the backbone and/or side chains of the basic polymer structure. This ability to fabricate many chemically different materials allows ready incorporation of a wide range of chemical diversity into the sensor elements, and also allows facile control over the electrical properties of the sensor elements through control over the composition of an individual sensor element in the array. Insulating organic materials can also be used and blended into the array in order to further increase the diversity in one embodiment of the invention. When insulators are added, commercial, off-the-shelf, organic polymers can provide the basic sensor components that respond differently to different analytes, based on the differences in polarity, molecular size, and other properties of the analyte in order to achieve the chemical diversity amongst array elements in the electronic nose sensors. Such insulators would include main-chain carbon polymers, main chain acyclic heteroatom polymers, main-chain heterocyclic polymers, and other insulating organic materials. Otherwise, these properties can be obtained by modification in the composition of the organic component of the sensor composition by use of capping agents on a colloidal metal part of the conductive phase, by use of different plasticizers added to otherwise compositionally identical sensor elements to manipulate their analyte sorption and response properties, by variation in the temperature or measurement frequency of the sensors in an array of sensors that are otherwise compositionally identical, or a combination thereof and with sensors that are compositionally different as well. The sensors in an a array can readily be made by combinatorial methods in which a limited number of feedstocks is combined to produce a large number of chemically distinct sensor elements.

One method of enhancing the diversity of polymer based conductor/conductor or conductor/semiconductor chemiresistors is through the use of polymer blends or copolymers (Doleman, et al., Anal. Chem. 70:2560–2654, 1998). Immiscible polymer blends may also be of interest because carbon black or other conductors can be observed to preferentially segregate into one of the blend components. Such a distribution of carbon black conduction pathways may result in valuable effects upon analyte sorption, such as the observance of a double percolation threshold. Binary polymer blend sensors can be prepared from a variety of polymers at incrementally different blend stoichiometries. Instead of manually fabricating twenty blends of varying composition, a spray gun with dual controlled-flow feedstocks could be used to deposit a graded-composition polymer film across a series of electrodes. Such automated procedures allow extension of the sensor compositions beyond simple binary blends, thereby providing the opportunity to fabricate chemiresistors with sorption properties incrementally varied over a wide range. In the fabrication of many-component blends, a combinatorial approach aided by microjet fabrication technology is one approach that will be known to those skilled in the art. For instance, a continuous jet fed by five separate feedstocks can fabricate numerous polymer blends in a combinatorial fashion on substrates with appropriately patterned sets of electrodes. Multiple nozzle drop-on-demand systems (multiple nozzle continuous jet systems are not as prevalent because of their greater complexity) may also be used. In this approach, each nozzle would be fed with a different polymer, each dissolved in a common solvent. In this manner, a large number of combinations of 10–20 polymers can be readily fabricated.

The resistors can include nanoparticles comprising a central core conducting element and an attached ligand, with these nanoparticles dispersed in a semi-conducting or conducting or insulating organic matrix. In certain embodiments, the nanoparticles have a metal core. Examples of metal cores include, but are not limited to, Au, Ag, Pt, Pd, Cu, Ni, AuCu and regions thereof. These metallic nanoparticles can be synthesized using a variety of methods. In one method of synthesis, a modification of the protocol developed by Brust et al. (the teachings of which are incorporated herein by reference), can be used. Using alkanethiolate gold clusters as an illustrative example, and not in any way to be construed as limiting, the starting molar ratio of $HAuCl_4$ to alkanethiol is selected to construct particles of the desired diameter. The organic phase reduction of $HAuCl_4$ by an alkanethiol and sodium borohydride leads to stable, modestly polydisperse, alkanethiolate-protected gold clusters having a core dimension of about 1 nm to about 100 nm. The nanoparticles range in size from about 1 nm to about 50 nm, but may also range in size from about 5 nm to about 20 nm.

In this reaction, a molar ratio of $HAuCl_4$ to alkanethiol of greater than 1:1 leads to smaller particle sizes, whereas a molar ratio of $HAuCl_4$ to alkanethiol less than 1:1 yield clusters which are larger in size. Thus, by varying the ratio of $HAuCl_4$ to alkanethiol, it is possible to generate various sizes and dimensions of nanoparticles suitable for a variety of analytes. Although not intending to be bound by any particular theory, it is believed that during the chemical reaction, as neutral gold particles begin to nucleate and grow, the size of the central core is retarded by the ligand monolayer in a controlled fashion. Using this reaction, it is then possible to generate nanoparticles of exacting sizes and dimensions.

In certain other embodiments, sensors are prepared as composites of "naked" nanoparticles and a semi-conducting or conducting organic material is added. As used herein, the term "naked nanoparticles" means that the core has no covalently attached ligands or caps. A wide variety of organic materials can be used in this embodiment. Preferred semi-conducting or conducting materials are organic polymers. Suitable organic polymers include, but are not limited to, polyaniline, polypyrrole, polyacetylene, polythiophene, polyEDOT and derivatives thereof. Varying the semi-conducting or conducting material types, concentration, size, etc., provides the diversity necessary for an array of sensors. In one embodiment, the conductor to semi-conducting or conducting organic material ratio is about 50% to about 90% (wt/wt).

A typical sensor array would produce a unique signature for every different analyte to which it was exposed. To construct such a system, it is necessary to include detectors that probe important, but possibly subtle, molecular parameters such as chirality. The term "chiral" is used herein to refer to an optically active or enantiomerically pure compound, or to a compound containing one or more asymmetric centers in a well-defined optically active configuration. For instance, because the active sites of enzymes are chiral, only the correct enantiomer is recognized as a substrate. Thus, pharmaceuticals having near enantiomeric purity are often many more times active than their racemic mixtures. However, many pharmaceutical formulations marketed today are racemic regions of the desired compound and its "mirror image." One optical form (or enantiomer) of a racemic region may be medicinally useful, while the other optical form may be inert or even harmful, as has been reported to be the case for thalidomide.

Plasticizers can also be used to obtain improved mechanical, structural, and sorption properties of the sensing films. Suitable plasticizers for use in the present invention include, but are not limited to, phthalates and their esters, adipate and sebacate esters, polyols such as polyethylene glycol and their derivatives, tricresyl phosphate, castor oil, camphor etc. Those of skill in the art will be aware of other plasticizers suitable for use in the present invention.

The plasticizer can also be added to an organic polymer forming an interpenetrating network (IPN) comprising a first organic polymer and a second organic polymer formed from an organic monomer polymerized in the presence of the first organic polymer. This technique works particularly well when dealing with polymers that are immiscible in one another, where the polymers are made from monomers that are volatile. Under these conditions, the preformed polymer is used to dictate the properties (e.g., viscosity) of the polymer-monomer region. Thus, the polymer holds the monomer in solution. Examples of such a system are (1) polyvinyl acetate with monomer methylmethacrylate to form an IPN of pVA and pMMA, (2) pVA with monomer styrene to form an IPN of pVA and polystyrene, and (3) pVA with acrylonitrile to form an IPN of pVA and polyacrylonitrile. Each of the example compositions would be modified by the addition of an appropriate plasticizer. More than one monomer can be used where it is desired to create an IPN having one or more copolymers.

In another embodiment, the sensor for detecting the presence of a analyte in a sample comprises a chemically sensitive resistor electrically connected to an electrical measuring apparatus where the resistor is in thermal communication with a temperature control apparatus. As described above, the chemically sensitive resistor(s) comprise regions of a conductive material and regions of a material which is compositionally different than the conductive material. The chemically sensitive resistor provides an electrical path through which electrical current may flow and a resistance (R) at a temperature (T) when contacted with a fluid comprising a chemical analyte.

In operation, the chemically sensitive resistor(s) of the sensor for detecting the presence of a chemical analyte in a fluid provide an electrical resistance ($R_m$) when contacted with a fluid comprising a chemical analyte at a particular temperature ($T_m$). The electrical resistance observed may vary as the temperature varies, thereby allowing one to define a unique profile of electrical resistances at various different temperatures for any chemical analyte of interest. For example, a chemically sensitive resistor, when contacted with a fluid comprising a chemical analyte of interest, may provide an electrical resistance $R_m$ at temperature $T_m$ where m is an integer greater than 1, and may provide a different electrical resistance Rn at a different temperature $T_n$. The difference between $R_m$ and $R_n$ is readily detectable by an electrical measuring apparatus.

As such, the chemically sensitive resistor(s) of the sensor are in thermal communication with a temperature control apparatus, thereby allowing one to vary the temperature at which electrical resistances are measured. If the sensor comprises an array of two or more chemically sensitive resistors each being in thermal communication with a temperature control apparatus, one may vary the temperature across the entire array (i.e., generate a temperature gradient across the array), thereby allowing electrical resistances to be measured simultaneously at various different temperatures and for various different resistor compositions. For example, in an array of chemically sensitive resistors, one may vary the composition of the resistors in the horizontal direction across the array, such that resistor composition in the vertical direction across the array remains constant. One may then create a temperature gradient in the vertical direction across the array, thereby allowing the simultaneous analysis of chemical analytes at different resistor compositions and different temperatures.

Methods for placing chemically sensitive resistors in thermal communication with a temperature control apparatus are readily apparent to those skilled in the art and include, for example, attaching a heating or cooling element to the sensor and passing electrical current through said heating or cooling element. The temperature range across which electrical resistance may be measured will be a function of the resistor composition, for example the melting temperature of the resistor components, the thermal stability of the analyte of interest or any other component of the system, and the like. For the most part, the temperature range across which electrical resistance will be measured will be about 10° C. to 80° C., preferably from about 22° C. to about 70° C. and more preferably from about 20° C. to 65° C.

In yet another embodiment, rather than subjecting the sensor to a direct electrical current and measuring the true electrical resistance through the chemically sensitive resistor (s), the sensor can be subjected to an alternating electrical current at different frequencies to measure impedance. Impedance is the apparent resistance in an alternating electrical current as compared to the true electrical resistance in a direct current. As such, the present invention is also directed to a sensor for detecting the presence of a chemical analyte in a fluid, said sensor comprising a chemically sensitive resistor electrically connected to an electrical measuring apparatus, said chemically sensitive resistor comprising regions of conductive material and regions of a material compositionally different than the conductive material and wherein the resistor provides an electrical impedance $Z_m$ at frequency m when contacted with a fluid comprising said chemical analyte, where m is an integer greater than 1 and m does not equal 0. For measuring impedance as a function of frequency, the frequencies employed will generally range from about 1 Hz to 5 GHz, usually from about 1 MHZ to 1 GHz, more usually from about 1 MHZ to 10 MHZ and preferably from about 1 MHZ to 5 MHZ. Chemical analytes of interest will exhibit unique impedance characteristics at varying alternating current frequencies, thereby allowing one to detect the presence of any chemical analyte of interest in a fluid by measuring $Z_m$ at alternating frequency m.

For performing impedance measurements, one may employ virtually any impedance analyzer known in the art. For example, a Schlumberger Model 1260 Impedance/Gain-Phase Analyzer (Schlumberger Technologies, Farmborough, Hampshire, England) with approximately 6 inch RG174 coaxial cables is employed. In such an apparatus, the resistor/sensor is held in an A1 chassis box to shield it from external electronic noise.

In still another embodiment of the present invention, one may vary both the frequency m of the electrical current employed and the temperature $T_n$ and measure the electrical impedance $Z_{m,n}$, thereby allowing for the detection of the presence of a chemical analyte of interest. As such, the present invention is also directed to a sensor for detecting the presence of a chemical analyte in a fluid, said sensor comprising a chemically sensitive resistor electrically connected to an electrical measuring apparatus and being in thermal communication with a temperature control apparatus, said chemically sensitive resistor comprising regions of conductive material and regions of a material compositionally different than the conductive material, wherein said resistor provides (1) an electrical path through the material, and (2) an electrical impedance $Z_{m,n}$ at frequency m and temperature $T_n$ when contacted with a fluid comprising said chemical analyte, where m and/or n is an integer greater than 1. For measuring impedance as a function of frequency and temperature, the frequencies employed will generally not be higher than 10 MHZ, preferably not higher than 5 MHZ. Chemical analytes of interest will exhibit unique impedance characteristics at varying alternating current frequencies and varying temperatures, thereby allowing one to detect the presence of any chemical analyte of interest in a fluid by measuring $Z_{m,n}$ at frequency m and temperature $T_n$.

In another procedure, one particular sensor composition can be used in an array and the response properties can be varied by maintaining each sensor at a different temperature from at least one of the other sensors, or by performing the electrical impedance measurement at a different frequency for each sensor, or a combination thereof.

An electronic nose for detecting an analyte in a fluid is fabricated by electrically coupling the sensor leads of an array of differently responding sensors to an electrical measuring device. The device measures changes in signal at each sensor of the array, preferably simultaneously and preferably over time. Preferably, the signal is an electrical resistance, although it could also be an impedance or other physical property of the material in response to the presence of the analyte in the fluid. Frequently, the device includes signal processing means and is used in conjunction with a computer and data structure for comparing a given response profile to a structure-response profile database for qualitative and quantitative analysis. Typically such a nose comprises usually at least ten, often at least 100, and perhaps at least 1000 different sensors though with mass deposition fabrication techniques described herein or otherwise known in the art, arrays of on the order of at least one million sensors are readily produced.

In one embodiment, the temporal response of each sensor (resistance as a function of time) is recorded. The temporal response of each sensor may be normalized to a maximum percent increase and percent decrease in signal which produces a response pattern associated with the exposure of the analyte. By iterative profiling of known analytes, a structure-function database correlating analytes and response profiles is generated.

The desired signals if monitored as dc electrical resistances for the various sensor elements in an array can be read merely by imposing a constant current source through the resistors and then monitoring the voltage across each resistor through use of a commercial multiplexable 20 bit analog-to-digital converter. Such signals are readily transmited and stored in a computer that contains a resident algorithm for data analysis and archiving. Signals can also be preprocessed either in digital or analog form; the latter might adopt a resistive grid configuration, for example, to achieve local gain control. In addition, long time adaptation electronics can be added or the data can be processed digitally after it is collected from the sensors themselves. This processing could be on the same chip as the sensors but also could reside on a physically separate chip or computer.

The invention will now be described in greater detail by reference to the following non-limiting examples.

EXAMPLES

A system acquires data from a sensor array when exposed to an unknown analyte, compares the sensor data for the unknown to data stored in a database, then provides the name of the analyte if the unknown matches a member of the database within some threshold accuracy. If no match is found the system returns the word "UNKNOWN". The system does four things: 1) collect response data from an array of chemiresistive vapor detectors exposed to an unknown analyte, 2) analyze the data and calculate the array response to the unknown, 3) compare the unknown's response values to values stored in a database, and, if a match is found that is within a desired accuracy, identifies the unknown. In addition, a database of the signatures for the analytes that are exposed to the sensor array is compiled, which can be used for historical analysis of change detection of that analyte as well as other transverse studies amongst groups of exposures to look for correlations between members of the group entries into the database.

The system was implemented with sensors consisting of conductive carbon black/polymer composite thin film chemiresistors that respond to analytes through a change in dc electrical resistance. The response was calculated as a differential relative resistance change ($\Delta R/R_b$) for each detector that occurs when the analyte molecules absorb into the films. The array consisted of 8 detectors each having a unique polymer component, each of which responds uniquely to an analyte vapor creating a pattern of response that is unique to that analyte vapor/detector array combination. The resistance data from the detector array were collected using a Keithely 2002 DMM coupled to a Keithely 7001 MUX that were controlled by a LabVIEW custom software program that integrated both units in to a real-time data acquisition system.

The data collection and analysis protocols were written as LabVIEW programs. These programs controlled the Keithely data acquisition system, stored the training sets, and compared unknowns to the training sets to make identifications. Additionally, a graphical user interface (GUI) was constructed consisting of dialog boxes, pull-down menus, operational buttons, and data output graphs. On the front panel of the GUI, the user defines the training analytes, sets an identification threshold, and can observe, in real-time, response histograms for both the training and unknown analytes.

The procedure for unknown identification is to first conduct training sets on the analytes of interest. The detector array was exposed to the test analytes in the same manner as will be used during subsequent identification attempts. The exposure established a baseline value for each of the detectors by observing on the computer screen the response by the array to baseline conditions. Once a steady-state response was achieved, a virtual-button was clicked on front panel of the GUI causing the program to save those response values and label them as baseline values ($R_b$ values). Concomitantly, the real-time response chart on the GUI re-zeros. The array was then exposed to the analyte of interest and the program calculated response values ($\Delta R/R_b$) for each detector in the array according to:

$$Q=(R-R_b)/R_b \qquad (1)$$

where $R_b$ is the baseline resistance value stored for each sensor when the user clicked the "zero" button on the GUI, R is the real-time resistance value for each resistor, and Q is defined as the response by a detector to an analyte. Q is calculated for every 1×8 array (8 detectors) of resistance values received from the Keithely system (approximately one set every second) and these response values are displayed on the GUI as a histogram, the abscissa of which corresponds to the detector number. When a sufficient equilibrium response is achieved, or whenever the user decides to terminate the analyte exposure, the Q values are labeled with the analyte descriptor and added to a training database for later use during identification tests. This procedure is done for each analyte trained into the system.

Once the training database is loaded, the user can identify analytes for which training data exists. The user places the array into baseline conditions and clicks the "Zero" button thus saving those $R_b$ values to be used in equation 1. Then the user places the array in the presence of the test analyte and the program calculates Q values. A sub-routine then calculates the shortest Euclidian distance between the unknown and each of the trained patterns according to $$[(Q_1 - T_{1,1})^2 + (Q_2 - T_{1,2})^2 + (Q_3 - T_{1,3})^2 + \ldots + (Q_n - T_{m,n})^2]^{0.5} = D_1 \quad (2)$$

$$[(Q_1 - T_{2,1})^2 + (Q_2 - T_{2,2})^2 + (Q_3 - T_{2,3})^2 + \ldots + (Q_n - T_{m,n})^2]^{0.5} = D_2$$

$$[(Q_1 - T_{3,1})^2 + (Q_2 - T_{3,2})^2 + (Q_3 - T_{3,3})^2 + \ldots + (Q_n - T_{m,n})^2]^{0.5} = D_3$$

$$\ldots$$

$$[(Q_1 - T_{m,1})^2 + (Q_2 - T_{m,2})^2 + (Q_3 - T_{m,3})^2 + \ldots + (Q_n - T_{m,n})^2]^{0.5} = D_m$$

where Q is the response value for the unknown analyte for each of n detectors in the array (in this case n=8), T is the response value in each training set for each of n detectors in the array, m is the number of training sets, $D_m$ is a scalar indicating the Euclidian distance between the Q values and the training set, $T_m$, in detector-space.

The minimum distance ($D_{m, min}$) is compared to a user-defined threshold. If $D_{m, min}$ is below the threshold, then the label of the training set m,min is output to the GUI. If $D_{m, min}$ is larger than the threshold, then the word "UNKNOWN" is output to the GUI. Additionally, the program can normalize the patterns and can save the data to a tab-delimited text file.

Once the array is cleared of the previous analyte, it can be placed back into the baseline conditions, the algorithm can again be "zeroed", and a subsequent identification test can begin immediately.

This hardware and software package is a stand-alone electronic nose that can detect and identify an analyte vapor without requiring data collection, manipulation, and synthesis by a user. The system allows for archiving and transmitting data to a remote location.

While the invention has been described in detail with reference to certain preferred embodiments thereof, it will be understood that modifications and variations are within the spirit and scope of that which is described and claimed.

What is claimed is:

1. A sensor array system for remote characterization of a gaseous or vapor sample, comprising:
    a plurality of sensors, wherein at least one sensor is an electrically conductive sensor comprising alternating regions of a conductive material and a material compositionally different than the conductive material between two conductive leads, wherein the sensor provides an electrical path through the regions of the conductive material and the regions of the compositionally different material, wherein the plurality of sensors provide a detectable signal when contacted by an analyte;
    a measuring apparatus, in communication with plurality of sensors capable of measuring the detectable signal;
    a transmitting device, in communication with the measuring apparatus for transmitting information corresponding to the detectable signal to a remote location via the Internet, fiber optic cable, and/or an air-wave frequency; and a computer comprising a resident algorithm capable of characterizing the analyte.

2. The system of claim 1, wherein the plurality of sensors further comprises a sensor selected from the group consisting of surface acoustic wave sensors, quartz crystal resonators, metal oxide sensors, dye-coated fiber optic sensors, dye-impregnated bead arrays, micromachined cantilever arrays, composites having regions of conducting material and regions of insulating organic material, composites having regions of conducting material and regions of conducting or semi-conducting organic material, chemically-sensitive resistor or capacitor films, metal-oxide-semiconductor field effect transistors, bulk organic conducting polymeric sensors, and any combination thereof.

3. The system of claim 1, wherein at least one sensor comprises regions of a conductive material and a conductive material compositionally different than the conductive material, wherein the sensor provides an electrical path through the regions of the conductive material and the regions of the compositionally different material, and wherein the conductivity changes upon adsorption with the analyte.

4. The system of claim 1, wherein at least one region of compositionally different material of one sensor is a different thickness than the region of compositionally different material of at least one other sensor.

5. The system of claim 1, wherein the compositionally different material is selected from the group consisting of polyanilines, an emeraldine salt of polyanilines, polypyrroles, polythiophenes, polyEDOTs, and derivatives thereof.

6. The system of claim 3, wherein the conductive material is selected from the group consisting of carbon black, Ag, Au, Pd, Cu, Ni, AuCu, and Pt.

7. The system of claim 5, wherein the at least one sensor further comprises an insulator or plasticizer.

8. The system of claim 3, wherein at least one other sensor comprises composites having regions of a conducting material and regions of a non-conducting organic material.

9. The system of claim 1, wherein the measuring apparatus converts the detectable signal to a digital representation of the detectable signal.

10. The system of claim 1, wherein the measuring apparatus converts the detectable signal to a digital profile representation of the detectable signal from each of the plurality of sensors.

11. The system of claim 1, wherein the sample is an environmental sample.

12. The system of claim 11, wherein the environmental sample is an air sample.

13. The system of claim 11, wherein the environmental sample is the headspace of a liquid sample.

14. The system of claim 1, wherein the sample is a biological sample.

15. The system of claim 14, wherein the biological sample is selected from the group consisting of a breath sample, a urine sample, a vaginal sample, a feces sample, a tissue sample and a blood sample.

16. The system of claim 14, wherein the biological sample is a breath sample.

17. The system of claim 1, wherein the data is analyzed by comparing the data to a database comprising a data profile from at least one previously-obtained detectable signal from a sample of known composition.

18. The system of claim 17, wherein the analyte in the sample is identified by matching the data to the data profile of a known composition in the database.

19. The system of claim 1, wherein the data is analyzed by comparing the data to a database containing data profiles from a plurality of detectable signals.

20. The system of claim 19, wherein each data profile in the database is associated with at least one identifier.

21. The system of claim 20, wherein the at least one identifier is selected from the group consisting of location, time, age, sex, disease state, temperature, sample source, sample type, organism, and ethnicity.

22. The system of claim 19, wherein the analyte is identified by a best match of the data to a data profile in the database and identifying any identifier associated with the data profile.

23. The system of claim 1, wherein the measuring apparatus is an electrical measuring device in electrical communication with the at least one sensor.

24. The system of claim 1, wherein the resident algorithm is a member selected from the group consisting of principal component analysis, Fisher linear analysis, neural networks, genetic algorithms, fuzzy logic, pattern recognition, and combinations thereof.

25. The system of claim 1, further comprising an information storage device coupled to the measuring apparatus and storing information in the information storage device.

26. The system of claim 23, wherein the measuring apparatus includes a digital-analog converter.

27. The system of claim 1, wherein the measuring apparatus is optimized to detect a member selected from the group consisting of electromagnetic energy, optical properties, resistance, capacitance, inductance, impedance and combinations thereof.

28. The system of claim 1, wherein the analyte is detected in an application which is a member selected from the group consisting of environmental toxicology, remediation, biomedicine, material quality control, food monitoring, agricultural monitoring, heavy industrial manufacturing, ambient air monitoring, worker protection, emissions control, product quality testing, oil/gas petrochemical applications, combustible gas detection, $H_2S$ monitoring, hazardous leak detection, emergency response and law enforcement applications, explosives detection, utility and power applications, food/beverage/agriculture applications, freshness detection, fruit ripening control, fermentation process monitoring and control, flavor composition and identification, product quality and identification, refrigerant and fumigant detection, cosmetic/perfume applications, fragrance formulation, chemical/plastics/pharmaceuticals applications, fugitive emission identification, solvent recovery effectiveness, hospital/medical applications, anesthesia and sterilization gas detection, infectious disease detection, breath analysis and body fluids analysis.

29. The system of claim 1, wherein the at least one sensor comprises 2 or more electrically conductive sensors.

30. The system of claim 1, wherein the plurality of sensors are electrically conductive sensors.

31. A system, comprising:
a plurality of sensor arrays at different remote locations, wherein each sensor array comprises a plurality of sensors;
a plurality of measuring apparata, in communication with each of the plurality of sensor arrays, wherein a measuring apparatus is capable of measuring a detectable change in a sensor array;
a plurality of transmitting devices, in communication with each measuring apparatus for transmitting information corresponding to the detectable signal to a remote location;
a computer comprising a resident algorithm capable of characterizing the analyte based upon the detectable signal; and a storage system at the remote location for storing and retrieving information related to the detectable signal.

* * * * *